US010503867B1

(12) United States Patent
Walker et al.

(10) Patent No.: US 10,503,867 B1
(45) Date of Patent: Dec. 10, 2019

(54) SYSTEM FOR INTERACTING WITH MEDICAL IMAGES

(71) Applicant: VIDISTAR, LLC, Greenville, SC (US)

(72) Inventors: Craig A. Walker, Greenville, SC (US); Michal Kostrzewa, Warsaw (PL); Steven Devann Johnson, Greenville, SC (US)

(73) Assignee: VIDISTAR, LLC, Greenville, SC (US)

( * ) Notice: Subject to any disclaimer, the term of this patent is extended or adjusted under 35 U.S.C. 154(b) by 794 days.

(21) Appl. No.: 15/017,469

(22) Filed: Feb. 5, 2016

Related U.S. Application Data

(63) Continuation-in-part of application No. 14/941,467, filed on Nov. 13, 2015, now Pat. No. 10,192,031, which is a continuation-in-part of application No. 13/507,195, filed on Jun. 11, 2012, now abandoned, which is a continuation-in-part of application No. 12/932,973, filed on Mar. 10, 2011, now Pat. No. 8,200,505, which is a continuation of application No.
(Continued)

(51) Int. Cl.
G06F 19/00 (2018.01)
G06F 3/0484 (2013.01)
G06F 17/24 (2006.01)
G06F 17/21 (2006.01)

(52) U.S. Cl.
CPC ........ *G06F 19/321* (2013.01); *G06F 3/04842* (2013.01); *G06F 3/04845* (2013.01); *G06F 17/212* (2013.01); *G06F 17/241* (2013.01)

(58) Field of Classification Search
CPC ........ G16H 15/00; G16H 40/20; G06F 19/00; G06F 19/321; G06F 19/328
See application file for complete search history.

(56) References Cited

U.S. PATENT DOCUMENTS 6,643,641 B1 11/2003 Snyder
7,283,857 B1 10/2007 Fallon et al.
(Continued)

OTHER PUBLICATIONS

Definition—corresponding—as downloaded from Google definitions (Year: 2018).*
(Continued)

Primary Examiner — Neal Sereboff
(74) Attorney, Agent, or Firm — Lindauer Law, PLLC

(57) ABSTRACT

Described are techniques for generating and modifying one or more diagrams based on one or more reports, and modifying the report(s) based on modifications to the diagram(s). The diagrams may include labels, graphical features, annotations, measurements, or other characteristics determined from the report. Visible indicia representing the characteristics may be automatically populated in the diagram, or certain characteristics may be displayed based on user input or preselected report content. Portions of the report may be mapped to regions of the diagram such that a user modification to a region of the diagram may result in a modification to a corresponding portion of the report, and a user modification to a portion of the report may result in a modification to a corresponding region of the diagram. Diagrams may include customized tools or operations for interacting with the diagram based on the structures depicted in the diagram.

20 Claims, 8 Drawing Sheets

Related U.S. Application Data

11/592,608, filed on Nov. 3, 2006, now abandoned, application No. 15/017,469, which is a continuation-in-part of application No. 14/081,054, filed on Nov. 15, 2013, now abandoned, which is a continuation-in-part of application No. 13/507,195, which is a continuation-in-part of application No. 12/932,973, which is a continuation of application No. 11/592,608.

(60) Provisional application No. 62/112,439, filed on Feb. 5, 2015, provisional application No. 61/727,364, filed on Nov. 16, 2012.

(56) References Cited

U.S. PATENT DOCUMENTS

| | | | |
|---|---|---|---|
| 2002/0143727 A1 | 10/2002 | Hu et al. | |
| 2003/0187689 A1 | 10/2003 | Barnes et al. | |
| 2004/0083217 A1 | 4/2004 | Brackett et al. | |
| 2004/0122844 A1 | 6/2004 | Malloy et al. | |
| 2004/0165700 A1 | 8/2004 | Batchelder et al. | |
| 2004/0252871 A1 | 12/2004 | Tecotzky et al. | |
| 2005/0149536 A1 | 7/2005 | Wildes et al. | |
| 2005/0273365 A1 | 12/2005 | Baumgartner et al. | |
| 2006/0004745 A1 | 1/2006 | Kuhn et al. | |
| 2006/0282447 A1 | 12/2006 | Hollebeek | |
| 2006/0285753 A1 | 12/2006 | Yamasaki | |
| 2007/0025606 A1 | 2/2007 | Gholap et al. | |
| 2007/0078674 A1 | 4/2007 | Weinberg et al. | |
| 2008/0109250 A1 | 5/2008 | Walker et al. | |
| 2009/0164474 A1 | 6/2009 | Noumeir | |
| 2009/0177637 A1 | 7/2009 | Hollebeek | |
| 2010/0008553 A1 | 1/2010 | Holmstrom | |
| 2011/0129131 A1 | 6/2011 | Avinash et al. | |
| 2011/0137132 A1* | 6/2011 | Gustafson | G16H 50/70 600/300 |
| 2012/0290321 A1* | 11/2012 | Hachmoller | G06F 19/328 705/3 |
| 2012/0323118 A1 | 12/2012 | Gopalakrishna et al. | |
| 2013/0339051 A1* | 12/2013 | Dobrean | G16H 15/00 705/3 |
| 2015/0066535 A1* | 3/2015 | Dobrean | G16H 15/00 705/3 |
| 2017/0083665 A1* | 3/2017 | Florin | G16H 15/00 |

OTHER PUBLICATIONS

Sereboff, Neal, "Non-final Office Action dated Feb. 19, 2016", U.S. Appl. No. 14/081,054, The United States Patent and Trademark Office, dated Feb. 19, 2016.

"Digital Imaging and Communications in Medicine (DICOM) Part 20: Transformation of DICOM to and from HL7 Standards", National Electrical Manufacturers Association, PS 3.20-2011, 2011, pp. 1-78.

"Introduction to Networking and the OSI Model", Pearson. Ch. 1, Jan. 3, 2001, pp. 1-22.

Clunie, David A., "Medical Image Format FAQ", Mar. 12, 2006.

HTTP Definition as downloaded from rhyshaden.com Feb. 2005 version of page.

Hussein, et al., "DICOM Structured Reporting Part 2. Problems and Challenges in Implementation for PACS Workstations", infoRAD, vol. 24, No. 3, RSNA, 2004, pp. 897-909.

Kalet, et al., "A declarative implementation of the DICOM-3 network protocol", Journal of Biomedical Informatics 36 (2003) pp. 159-176. Received Feb. 21, 2003.

Mhiri, et al., "An Ontology Visualization Tool for Indexing DICOM Structured Reporting (SR) Documents", CRIP5, University of Paris V, 75006 Paris, France.

Mhiri, et al., "Ontology Usability Via a Visualization Tool for the Semantic Indexing of Medical Reports (DICOM SR)", A. Holzinger (Ed.): USAB 2007, LNCS 4799, pp. 409-410, 2007.

Noumeir, Rita, "Benefits of the DICOM Structured Report", Journal of Digital Imaging, vol. 19, No. 4 (December), 2006: pp. 295-306.

Oracle, "Oracle9i Reports, Building Reports Release 9.0", Part No. B10310-01, Oct. 2002.

Sereboff, Neal, "Final Office Action dated Jul. 13, 2015", U.S. Appl. No. 13/507,195, The United States Patent and Trademark Office, dated Jul. 13, 2015.

Sereboff, Neal, "Final Office Action dated Nov. 10, 2010", U.S. Appl. No. 11/592,608, The United States Patent and Trademark Office, dated Nov. 10, 2010.

Sereboff, Neal, "Non-Final Office Action dated Apr. 21, 2010", U.S. Appl. No. 11/592,608, The United States Patent and Trademark Office, dated Apr. 21, 2010.

Sereboff, Neal, "Non-Final Office Action dated Mar. 19, 2015", U.S. Appl. No. 13/507,195, The United States Patent and Trademark Office, dated Mar. 19, 2015.

Sereboff, Neal, "Non-Final Office Action dated Nov. 25, 2011", U.S. Appl. No. 12/932,973, The United States Patent and Trademark Office, dated Nov. 25, 2011.

Sereboff, Neal, "Notice of Allowance dated Mar. 23, 2012", U.S. Appl. No. 12/932,973, The United States Patent and Trademark Office, dated Mar. 23, 2012.

Sun Microsystems, Inc., "JAVA™ Web Start Overview", White Paper, May 2005.

Tachibana, et al., "Design and Development of a Secure DICOM-Network Attached Server". Originally published in Jpn J Radiol Technol, 62(4), (2006), 529-538.

Toffoli, Giulio, "iReport User Manual, version 1.0", copyright 2004.

VidiStar, "Presenting . . . VidiStars Standalone Viewer™", 2004.

Walker, Craig A., "VidiStar, LLC Receives the 2013 InnoVision Award for Technology Development", VidiStar LLC DICOM PACS Online Medical Imaging Software, Nov. 8, 2013. [retrieved on Aug. 18, 2015]. Retrieved from the Internet: <http://www.vidistar.com/vidistar-llc-receives-the-2013-innovision-award-for-technology-development>.

\* cited by examiner

SYSTEM FOR INTERACTING WITH MEDICAL IMAGES

CROSS-REFERENCE TO RELATED APPLICATIONS

This application claims priority to U.S. provisional application 62/112,439, filed Feb. 5, 2015.

This application also claims priority to and is a continuation-in-part of U.S. application Ser. No. 14/941,467, filed Nov. 13, 2015. Application Ser. No. 14/941,467 in turn claims priority to U.S. application Ser. No. 13/507,195, filed Jun. 11, 2012, now abandoned. Application Ser. No. 13/507,195 in turn claims priority to U.S. application Ser. No. 12/932,973, filed Mar. 10, 2011, which issued as U.S. Pat. No. 8,200,505 on Jun. 12, 2012. Application Ser. No. 12/932,973 in turn claims priority to U.S. application Ser. No. 11/592,608, filed Nov. 3, 2006, now abandoned.

This application also claims priority to and is a continuation-in-part of U.S. application Ser. No. 14/081,054, filed Nov. 15, 2013. Application Ser. No. 14/081,054 in turn claims priority to U.S. provisional application 61/727,364, filed Nov. 16, 2012. Application Ser. No. 14/081,054 also claims priority to U.S. application Ser. No. 13/507,195, filed Jun. 11, 2012, now abandoned. Application Ser. No. 13/507,195 in turn claims priority to U.S. application Ser. No. 12/932,973, filed Mar. 10, 2011, which issued as U.S. Pat. No. 8,200,505 on Jun. 12, 2012. Application Ser. No. 12/932,973 in turn claims priority to U.S. application Ser. No. 11/592,608, filed Nov. 3, 2006, now abandoned.

U.S. Pat. No. 8,200,505 (entitled "System and method for creating and rendering DICOM structured clinical reporting via the internet", filed Mar. 10, 2011); U.S. application 62/112,439 (entitled "System for interacting with medical images", filed Feb. 5, 2015); U.S. application Ser. No. 14/941,467 (entitled "System for extracting information from DICOM structured reports", filed Nov. 13, 2015); U.S. application Ser. No. 13/507,195 (entitled "Systems and methods for data mining of DICOM structured reports", filed Jun. 11, 2012); U.S. application Ser. No. 12/932,973 (entitled "System and method for creating and rendering DICOM structured clinical reporting via the internet", filed Mar. 10, 2011); U.S. application Ser. No. 11/592,608 (entitled "System and method for creating and rendering DICOM structured clinical reporting via the internet", filed Nov. 3, 2006); U.S. application Ser. No. 14/081,054 (entitled "Methods and systems for analyzing medical image data", filed Nov. 15, 2013; and U.S. application 61/727,364 (entitled "Systems and methods for data mining of nuclear medicine images", filed Nov. 16, 2012) are incorporated by reference herein in their entirety.

BACKGROUND

Medical images of numerous types may be produced using a variety of technologies. The information contained in these images may be output in various ways. Digital Imaging and Communications in Medicine (DICOM) standards for handling, storing, printing, and transmitting information relating to medical imaging may facilitate the communication of information between different parties.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
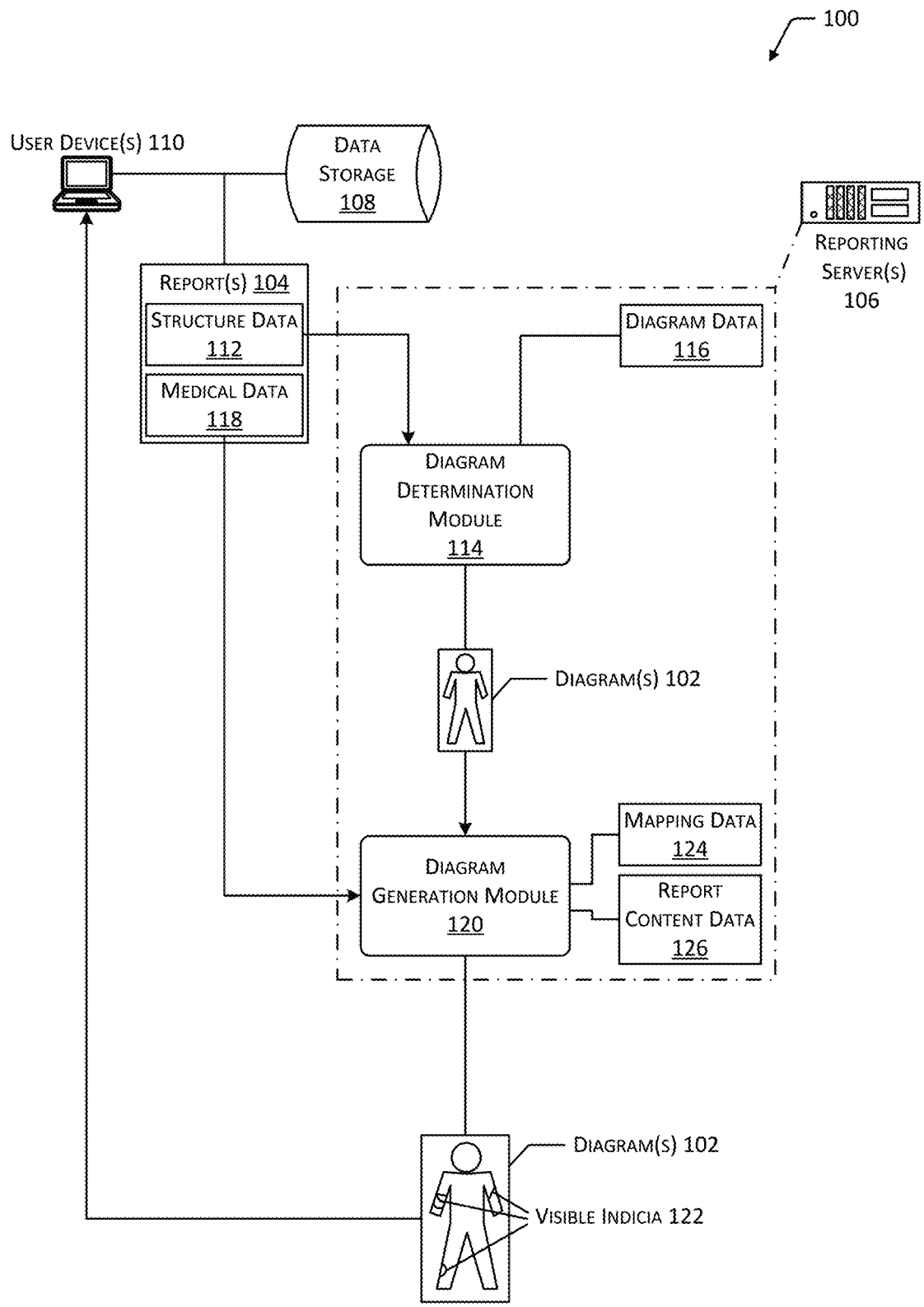
FIG. 1 is depicts an example system for determining one or more diagrams based on one or more reports.

While implementations are described in this disclosure by way of example, those skilled in the art will recognize that the implementations are not limited to the examples or figures described. It should be understood that the figures and detailed description are not intended to limit implementations to the particular form disclosed, but on the contrary, the intention is to cover all modifications, equivalents, and alternatives falling within the spirit and scope as defined by the appended claims. The headings used in this disclosure are for organizational purposes only and are not meant to limit the scope of the description or the claims. As used throughout this application, the word "may" is used in a permissive sense (i.e., meaning having the potential to) rather than the mandatory sense (i.e., meaning must). Similarly, the words "include," "including," and "includes" mean including, but not limited to.

DETAILED DESCRIPTION

The advent of DICOM standards has led to a standardization of clinical reports to a format that outlines the basic content of the reports for medical interpretation and analysis. Previously, difficulties existed when attempting to share data between proprietary information systems and DICOM imaging modalities or to search or query such data. For example, different medical devices may generate different types of data (e.g., alphanumeric data, image data, etc.) using layouts, data structures, metadata, measurements, and so forth that are unique to that particular device. Continuing the example, a report received from a medical device may include one or more images, including medical images as well as images of text reflecting medical findings, patient demographic information, date and time of a study, a performing examiner's name, an interpreting physician's name, reimbursement code(s), study quality, clinical assessment, medical findings, diagnostic measurements, diagnostic data, vital information, impressions, and so forth. Optical character recognition (OCR) or other types of image recognition may be used to extract values from such images that may be used to populate a standardized report template. One example method for receiving input data, such as medical images, processing the input files, and generating structured reports, is described in greater detail in U.S. Pat. No. 8,200,505.

While a report may include fields that contain values indicative of medical information, the text of the report, alone, may provide only a portion of the information that may be determined from a patient study. For example, while the text of a report may indicate the presence of a stent or a lesion in a particular artery, the precise location of that stent, the size and shape of the lesion, and so forth, may be more accurately or more completely represented using an image. As such, a medical report may include one or more diagrams that may depict information using visible indicia, such as graphical representations of stents, lesions, or other medical features, devices, or structures. Implementations described herein may include techniques for generating one or more images, such as medical images or a schematic diagrams, based on one or more structured reports, generating reports based on one or more images, modifying reports based on modifications to images, and modifying images based on modifications to reports.

To generate a diagram, a report may be accessed from one or more memories (e.g., computer-readable storage media (CRSM) or other types of data storage) or received via one or more networks. The report may include structure data indicative of medical structures, such as body parts, body systems (e.g., circulatory), and so forth. For example, the body parts or systems associated with a report may be determined from a header, a title, a file name, one or more fields present in the report, one or more values within particular fields of the report, and so forth. The report may also include medical data indicative of values or characteristics associated with medical structures. For example, one or more values associated with a particular vessel, medical device, foreign body, or other type of object may indicate linear dimensions, flow rates, volumes, and so forth associated with the object. As another example, medical data may indicate the presence or location of a medical device, such as a stent, a medical condition, such as vessel narrowing or a lesion, and so forth, associated with a particular medical structure.

Based on at least a portion of the data in the report, a diagram suitable for use with the report may be determined. In some implementations, correspondence may be determined between at least a portion of the repot and diagram data that associates medical structures with diagrams. For example, metadata associated with a report, a title, a file name, a header, the presence of one or more particular fields, the presence of one or more particular vales, and so forth, may indicate that a report is associated with a particular medical structure, such as a patient's circulatory system. The diagram data may include one or more corresponding diagrams that depict circulatory systems, stored in association with data indicative of circulatory medical structures. Based on correspondence between the report and the diagram data, one or more particular diagrams that depict at least a portion of the circulatory system may be determined. In some implementations, multiple diagrams that correspond to a report may be determined. For example, a series of diagrams may depict various views of a particular vessel. In other implementations, a single diagram may correspond to a single report. In still other implementations, a single diagram may correspond to multiple reports. For example, data from multiple reports, each pertaining to different portions of the circulatory system, may be reflected in a single diagram representing the entire circulatory system.

To populate the diagram with one or more visible indicia of the medical data in the report, mapping data may be used, which associates one or more regions of the diagrams with corresponding portions of the report. For example, a portion of the report that includes text indicative of a medial impression, such a width of the right common iliac artery, may correspond to a particular region of a diagram that depicts the right common iliac artery. As another example, a portion of the report that includes text indicating the presence of a medical feature, such as a lesion in right circumflex artery, may correspond to a particular region of a diagram that depicts the right circumflex artery. Visible indicia corresponding to at least a portion of the medical data of the report may be generated in the diagram.

In some implementations, the particular indicia that are provided to a diagram may be determined based on report content data. For example, report content data may include one or more images representative of particular medical features, such as stents, bypasses, grafts, lesions, narrowing, and so forth. Based on the report content data and the type of medical feature indicated in the report, a particular image may be used in the diagram to represent the medical feature. The report content data may also include layout or template data indicative of a position at which a visible indication is to be placed. For example, a numerical value indicative of a dimension associated with the right common iliac artery may be positioned proximate to the location of the right common iliac artery in the diagram, at a particular position indicated in the report content data. The report content data may also include an indication of the particular medical data to be included in the diagram. A diagram may include all medical data that may be determined from a report or only a portion of the medical data. For example, the report content data may indicate particular fields, values, or types of medical data to be included in the diagram. Continuing the example, the report content data may indicate that vessel widths are to be included in the diagram, while vessel flow rates are to be excluded. In some implementations, the report content data may be modified based on user input. For example, a user may select particular medical data from a report for inclusion in a diagram. In some implementations, the report content data may also indicate particular graphical layers that may be associated with features of the diagram. For example, text annotations may be provided to a first layer of the diagram while medical structures are provided to a different layer. A user interacting with the diagram may suppress one or more layers from view, specifically interact with selected layers, and so forth.

The generated diagram may be stored in association with a report. In some implementations, reports may be queried based on the presence or absence of a diagram, the presence or absence of particular indicia or features within a diagram, and so forth.

In some implementations, a report may be automatically modified based on user input interacting with a diagram. Similarly, a diagram may be modified based on user interactions with a report. For example, if a user modifies a value located in a particular field of a report, mapping data may be used to determine a corresponding region of the diagram. A visible indication of the value in the region of the diagram may be added, removed, or modified based on the user modification to the report. As another example, a user may add, remove, or modify a visible indication in a diagram, and a corresponding change may be populated into a report. Continuing the example, a user may modify a text label within a diagram that indicates a particular value for the width of an occlusion. Based on the modification to the text label, a modified value may be added to a corresponding field of the report. As yet another example, a user may select a particular tool indicative of a medical feature, such as a lesion, a graft, or a bypass. The user may then select portions of the diagram to be associated with the medical feature. Continuing the example, a user may draw a lesion, select endpoints of a bypass, and so forth. In some implementations, the user may input parameters associated with the medical feature, such as text or mouse-driven selections indicative of dimensions of the medical feature. Parameters may also be determined based on the user interactions with the diagram, such as selection of the locations of bypass endpoints or the dimensions and location of a lesion. Values indicative of these user interactions with the diagram may be added to corresponding locations in the report, or existing values in the report may be modified based on the user interactions.

FIG. 1 depicts an example system 100 for determining one or more diagrams 102 based on one or more reports 104. One or more reporting servers 106 may be used to determine reports 104 and generate diagrams 102. The reporting server(s) 106 may include any number and any type of computing device(s), such as mobile devices, set-top boxes, tablet computers, personal computers, wearable computers, servers, and so forth. In some implementations, the reporting server(s) 106 determine an existing report 104 from one or more data storage media 108. For example, data storage media 108 may include one or more electronic storage media, magnetic storage media, optical storage media, quantum storage media, mechanical storage media, or other types of CRSM. The data storage media 108 may use a flat file, database, linked list, tree, executable code, script, or other data structures to store information. While FIG. 1 depicts the data storage media 108 remote from the reporting server(s) 106, other implementations may include data storage 108 integrated with or in direct communication with the reporting server(s) 106. In other implementations, the reporting server(s) 106 may receive a report 104 from a user device 110 or medical imaging or reporting device, or otherwise determine or access the report 104 associated with the user device 110. User device(s) 110 may include any number and any type of computing device including, without limitation, the types of computing devices described with reference to the reporting server(s) 106. A user device 110 may provide a report 104 directly to the reporting server(s) 106, or the user device 110 may provide the report to the data storage media 108, from which the reporting server(s) 106 may access the report 104. In still other implementations, the reporting server(s) 106 may determine multiple reports 104 from one or multiple sources. The reporting server(s) 106 may communicate with various user devices 110 and data storage media 108 via one or more networks, such as local area networks (LANs), wireless LANs, wide area networks (WANs), wireless WANs, and so forth.

A report 104 may include structure data 112 indicative of one or more medical structures. For example, structure data 112 may include a title, header, file type, or file name, associated with the report 104, that indicates one or more particular body parts, body systems, and so forth. As another example, structure data 112 may include metadata associating the report 104 with particular medical structures. As yet another example, structure data 112 may include one or more fields, nodes, or other data structures present in the report 104, or one or more particular values within one or more of the fields, which may indicate a medical structure associated with the report. Continuing the example, the presence of one or more fields associated with flow rates of vessels may indicate that the report 104 pertains to a patient's circulatory system.

A diagram determination module 114 associated with the reporting server(s) 106 may determine one or more diagrams 102 that correspond to the report 104 based at least in part on the structure data 112. For example, the diagram determination module 114 may access diagram data 116 that associates particular diagrams 102 with corresponding structure data 112. Continuing the example, the diagram data 116 may associate a particular report title or header, particular report metadata, particular report fields or values, and so forth, with particular diagrams 102. Based on correspondence between at least a portion of the report(s) 104 and at least a portion of the diagram data 116, the diagram determination module 114 may determine one or more diagrams 102 associated with medical structures indicated by the structure data 112. For example, diagrams 102 may depict one or more portions of body systems (e.g., skeletal, nervous, muscular, circulatory, and so forth), particular regions of the body (e.g., upper right quadrant), particular body parts (e.g., left leg, head, torso), particular anatomical elements (e.g., particular vessels, organs, etc.), and so forth. In some implementations, multiple diagrams 102 that correspond to a particular report 104 may be determined. For example, multiple diagrams 102, each depicting a particular view of a medical structure, may be used in conjunction with a report 104 associated with that medical structure. In other implementations, a single diagram 102 may correspond to multiple reports 104. For example, multiple studies associated with a patient may result in the generation of multiple reports 104, each pertaining to a particular portion of the patient's circulatory system. A corresponding diagram 102 may depict the entire circulatory system and include data from multiple reports 104. In still other implementations, a single diagram 102 may correspond to a single report 104.

The report 104 may also include medical data 118 indicative of medical findings, impressions, values, and so forth. For example, medical data 118 may indicate the presence or absence of particular medical conditions or objects, such as narrowed vessels, lesions, occlusions, stents, grafts, bypasses, and so forth, and the location of such conditions or objects. Medical data 118 may also include one or more measurements or other values that correspond to particular fields of the report 104. For example, medical data 118 may include a measurement of the width of a vessel that may be determined from one or more field or nodes in the report 104. In some implementations, medical data 118 may include alphanumeric data, such as text indicative of medical impressions. In other implementations, medical data 118 may include image data. For example, a report 104 may include one or more scans of a patient or other types of images, images of text recorded by medical personnel that may be analyzed using OCR, or other types of image data. In still other implementations, a report 104 may include audio data. For example, a report may include recorded speech or other audible components recorded by medical personnel that may be analyzed using speech-to-text or other speech recognition or audio recognition techniques. Example methods for determining and utilizing appropriate plug-ins for extracting values from reports are described in U.S. Pat. No. 8,200,505.

A diagram generation module 120 associated with the reporting server(s) 106 may provide one or more visible indicia 122 to the determined diagram(s) 102 indicative of at least a portion of the medical data 118. The diagram determination module 120 may access mapping data 124 that associates particular portions of the report(s) 104 to particular regions of the diagram(s) 102. For example, the mapping data 124 may associate a portion of the report 104 that contains measurements of the left common iliac artery with a region of the diagram 102 proximate to a depiction of the left common iliac artery. Based on the mapping data 124, the diagram generation module 120 may provide a visible indication 122 indicative of the measurement at a location in the diagram 102 proximate to the related anatomical structure. As another example, the mapping data 124 may associate one or more portions of a report 104 with regions of a diagram 102 remote from or independent of depictions of particular anatomical structures. Continuing the example, medical data 118 indicative of a patient's name, a report title, an examining physician, reporting codes, and so forth may be provided to regions of the diagram 102 that do not overlap depictions of anatomical structures.

The diagram generation module 120 may also access report content data 126 indicative of particular characteristics to be applied to the diagram 102 and particular portions of medical data 118 to be indicated using the visible indicia 122. For example, the report content data 126 may indicate particular symbols, images, colors, patterns, or other graphical elements to be used to indicate particular types of medical data 118. The report content data 126 may also indicate particular medical data 118 or categories of medical data 118 to be included in or omitted from a diagram 102. For example, the report content data 126 may indicate that text labels of particular vessels are to be excluded from a diagram 102 while text labels indicating dimensional measurements of the vessels are to be included. As another example, the report content data 126 may indicate the style and position of text labels. In some implementations, at least a portion of the report content data 126 may be determined based on user input. For example a user associated with the user device 110 may select one or more fields or values of a report 104. The diagram generation module 120 may provide visible indicia 122 to the diagram based on the medical data 118 corresponding to the selected fields or values. Continuing the example, a user may select a portion of the report 104 describing the placement of a bypass or graft. Responsive to the user selection, the diagram generation module 120 may provide the diagram 102 with a visible indication 122 corresponding to the bypass or graft.

A generated diagram 102 that includes one or more visible indicia 122 may be stored in association with a report 104 for subsequent access, querying, and so forth. For example, responsive to a report 104 received from a user device 110, one or more diagrams 102 may be provided to the user device 110 to accompany the report 104.

Figure 2:
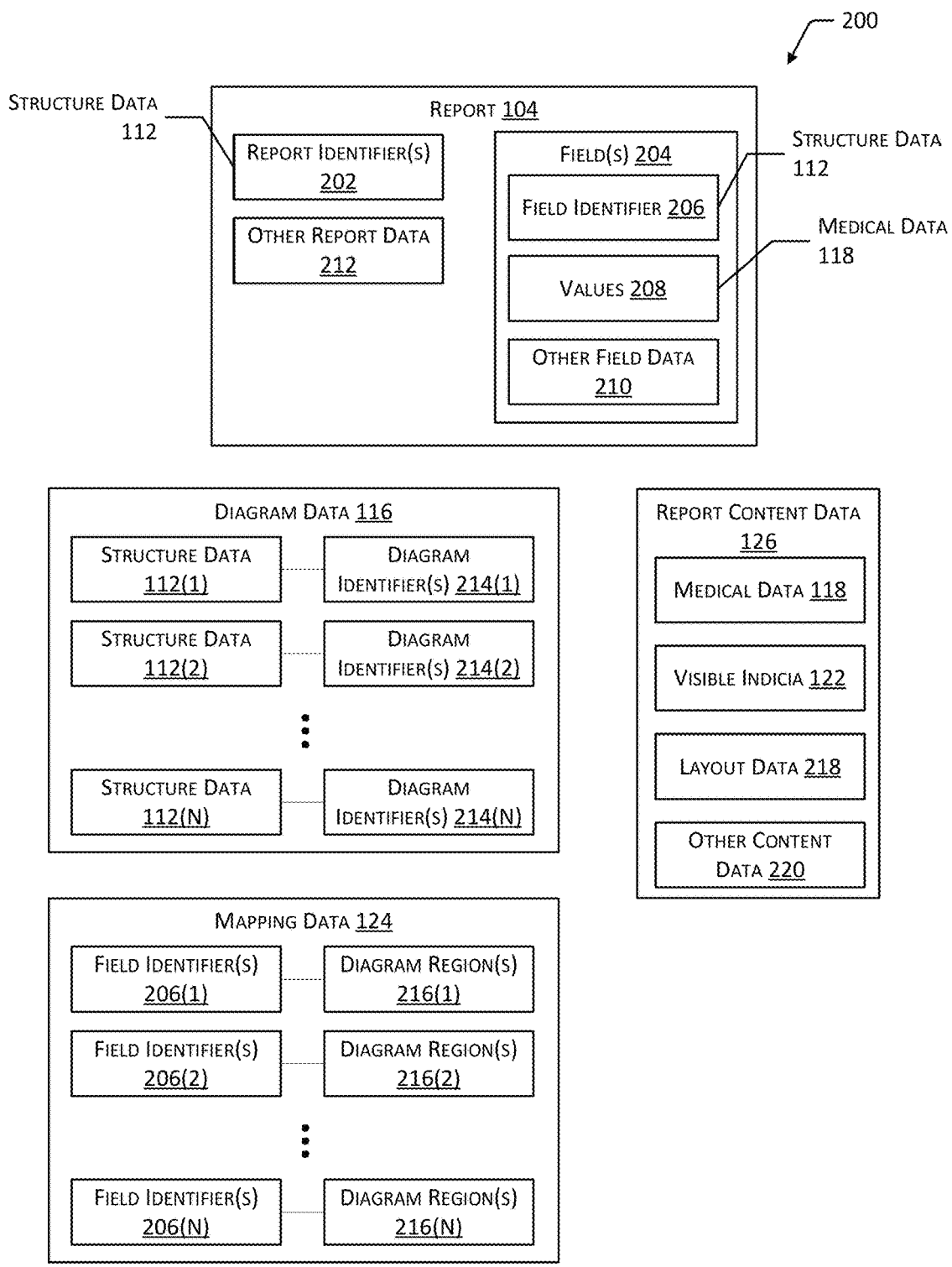
FIG. 2 is a block diagram depicting an example report, diagram data, mapping data, and report content data.

FIG. 2 is a block diagram 200 depicting an example report 104, diagram data 116, mapping data 124, and report content data 126. Reports 104 may include any manner of clinical report or other type of report, having any format, layout, or standard, including without limitation the DICOM standard. A report 104 may include one or more report identifiers 202, such as a name, title, file name, header, metadata, or other data indicative of a particular report 104 that may be used to differentiate the report 104 from other reports 104 or other types of data. In some implementations, one or more report identifiers 202 may indicate a type, category, or other characteristic associated with the report. For example, a title associated with an adult echocardiography study may include the alphanumeric string "Adult Echocardiography Procedure Report", while a title associated with a vascular ultrasound study may include the alphanumeric string "Vascular Ultrasound Procedure Report". In some implementations, one or more of the report identifiers 202 may include codes corresponding to the DICOM standard. For example, the title of a report 104 may include a coded value indicative of the nature of the report 104. Continuing the example, a report 104 may be identified by a code, such as "125200, DCM," Adult Echocardiography Procedure Report").

A report 104 may also include one or more fields 204 configured to contain information. Each field may include one or more field identifiers 206 indicative of a name, title, header, or type associated with the field 204. At least a portion of the fields 204 may contain one or more values 208, which may include alphanumeric data, image data, audio data, and so forth. In some implementations, the report identifier 202 of a report 104 may be a value 208 associated with a field 204. For example, a report 104 may include a field 204 configured to contain a title or header of the report 104. As another example, a report 104 may include a DICOM structured report, and the root or parent node of the DICOM structured report may include a value 208 indicative of the title of the report 104. In other implementations, the report identifier 202 may be separate from the fields 204.

Fields 204 of a report 104 may include any manner of data structure. For example, in a DICOM structured report, nodes may be arranged in a tree or graph structure in which certain nodes are associated with or depend from certain other nodes. Other data structures may include databases, tables, and so forth. At least a portion of the fields 204 may include one or more field identifiers 206, which may include any manner of alphanumeric data, image data, audio data, and so forth, that may be used to differentiate a particular field 204 from other fields 204. In some implementations, a field identifier 206 may indicate a type or category corresponding to the value(s) 208 contained in a field 204. For example, a field identifier 206 may indicate that a particular field 204 contains numeric data, text, image data, and so forth. If the report 104 is a DICOM structured report, the field identifier 206 may indicate that a particular node is a container node. Values 208 within the fields 204 may include any manner of alphanumeric data, image data, or audio data. For example, a value 208 may include a Boolean result (e.g., "True", "False", "Yes", "No", "Present", "Absent"), a name, text representative of medical findings, numeric measurements, images, references to portions of images, recorded audio, and so forth.

Other field data 210 may include data indicative of characteristics of a field 204, such as a type or category of the field 204, a data structure of the field 204, a type or category associated with the value 208, a particular data type of the value 208, units of measurement, format an style characteristics of a field 204, and so forth. In some implementations, other field data 210 may indicate relationships between one or more fields 204 of a report 104. For example, fields 204 may depend from one another in a parent-child relationship. As another example, the report 104 may include a DICOM structured report, and field relationships may include DICOM relationships such as "contains", "has observation context", "has acquisition context", "has concept modifier", "has properties", "inferred from", or "selected from".

Other report data 212 associated with a report 104 may include data or metadata indicative of the author of a report 104, the date or time at which a report 104 was generated, modified, completed, or verified, version information associated with the report 104, a type or category associated with the report 104, and so forth. Other report data 212 may also include attributes that identify the report 104 as a report 104 for differentiating the report 104 from other types of files or data. Other report data 212 may also indicate relationships between reports 104. For example, a first report 104 may include a preliminary patient study signed by a technician, while a second report 104 may include a subsequent version of the first report 104, reviewed, modified, and signed by a physician. Other report data 212 may further indicate relationships between reports 104 and diagrams 102.

As described with regard to FIG. 1, certain elements of the report 104 may be used as structure data 112 for determining medical structures associated with the report 104. For example, report identifiers 202 and field identifiers 206 may indicate an anatomical structure, body system, or other medical structure associated with the report 104. In some implementations, one or more values 208 may also be used as structure data 112. For example, a report 104 that includes a first range of values 208 may be associated with a study of circulatory vessels, while a report 104 that includes a second range of values 208 may be associated with a study of particular organs. Certain elements of the report 104 may also be used as medical data 118 for determining medical conditions, objects, and so forth associated with the report 104. For example, one or more values 208 in a report 104 may indicate medical measurements, findings, impressions, and so forth. In some implementations, other elements of the report 104 may also be used as medical data 118. For example, the presence of particular field identifiers 206 associated with vessel flow rates may indicate that a report 104 relates to a patient experiencing certain vascular conditions independent of the values 208 within the fields 204.

Diagram data 116 may be used to determine particular diagrams 102 that correspond to structure data 112 determined from one or more reports 104. For example, a diagram 102 depicting one or more portions of a circulatory system may correspond to a report 104 pertaining to a vascular study. Based on structure data 112 determined from the report 104 that indicates that the report pertains to such a study, one or more corresponding diagrams 102 depicting elements of the circulatory system may be determined. As such, the diagram data 116 may include indications of structure data 112 stored in association with diagram identifiers 214.

As described with regard to FIG. 1, structure data 112 may include data indicative of a medical structure associated with the report 104. For example, a report identifier 202 (e.g., a name, title, file name, and so forth), the presence or absence of one or more fields 204, or the presence or absence of one or more values 208 may indicate one or more medical structures associated with the report 104. Diagram identifiers 214 may include any manner of alphanumeric, image, or audio data, such as a name, title, file name, header, metadata, or other data indicative of a particular diagram 102, that may be used to differentiate the diagram 102 from other diagrams 102 or other types of data. In some implementations, the diagram identifiers 214 may indicate a type, category, or medical structure corresponding to the diagram 102. For example, a diagram identifier 214 may include a title, header, file name, or metadata indicative of one or more medical structures.

Structure data 112 stored in association with one or more diagram identifiers 214 may indicate correspondence between the medical structure depicted in the associated diagram 102 and the medical structure indicated by the structure data 112. For example, FIG. 2 depicts first structure data 112(1) stored in association with one or more first diagram identifiers 214(1), second structure data 112(2) stored in association with one or more second diagram identifiers 214(2), and any number of additional structure data 112(N) stored in association with any number of additional diagram identifiers 214(N). In some implementations, a single diagram identifier 214 may correspond to a single set of structure data 112. In other implementations, multiple diagram identifiers 214 may correspond to a single set of structure data 112. In still other implementations, a single diagram identifier 214 may correspond to multiple sets of structure data 112.

Mapping data 124 may associate particular portions of a report 104 (e.g., fields 204) with particular diagram regions 216. For example, the mapping data 124 may associate a field identifier 206 corresponding to a field 204 relating to the dimensions of an aorta with a diagram region 216 of a particular diagram 102 proximate to a depiction of the aorta. As discussed previously, field identifiers 206 or other structure data 112 may indicate a medical structure that corresponds to a particular field 204. A diagram 102 that depicts one or more medical structures may include various diagram regions 216, which may include indications of coordinates, pixels, or other methods for differentiating particular sections of a diagram 102 from other sections. For example, data or metadata associated with a diagram 102 may include an indication of one or more diagram regions 216 and coordinates that correspond to the diagram region(s) 216. At least a portion of the diagram regions 216 associated with a diagram 102 may correspond to one or more field identifiers 206 of a report, as indicated in the mapping data 124. The mapping data 124 may therefore be used to provide an indication of a value 208 contained within a particular field 204 to a diagram region 216 that corresponds to the field 204.

For example, FIG. 2 depicts one or more first field identifiers 206(1) stored in association with data indicative of one or more first diagram regions 216(1), one or more second field identifiers 206(2) stored in association with data indicative of one or more second diagram regions 216(2), and any number of additional field identifiers 206(N) stored in association with any number of additional diagram regions 216(N). In some implementations, a single field identifier 206 may correspond to a single diagram region 216. In other implementations, multiple field identifiers 206 may correspond to a single diagram region 216. In still other implementations, a single field identifier 206 may correspond to multiple diagram regions 216.

Report content data 126 may indicate particular medical data 118 to be represented in a diagram 102, particular medical data 118 to be excluded from a diagram 102, and the manner in which particular medical data 118 is to be represented in a diagram 102. For example, the report content data 126 may indicate particular field identifiers 206 or values 208 of a report 104 for inclusion in a diagram 102. Continuing the example, report content data 126 may indicate that values 208 determined from fields 204 containing measurements relating to vessel widths are to be included in a diagram 102. As another example, report content data may indicate that all lesions, occlusions, or narrowing regions of vessels having a width of greater than 2 mm are to be included in a diagram 102.

The report content data 126 may also include data indicative of one or more visible indicia 122 by which particular medical data 118 may be represented in a diagram 102. For example, the report content data 126 may indicate particular graphic elements, patterns, symbols, fonts, colors, and so forth that may be used to represent values 208 determined from particular fields 204. Continuing the example, the report content data 126 may indicate that bypasses are to be represented using a blue arc, narrowed vessels are to be represented using opposing red arcs, stenosis and occlusion is to be represented as shaded black regions, grafts are to be represented using cross-hatching, text labels indicating vessel names are to be represented using a first font type and size, text labels indicating vessel measurements are to be represented using a second font type and size, and so forth. The report content data 126 may also include layout data 218 indicative of the placement, spacing, or other formatting elements associated with the visible indicia 122 or other content of a diagram 102. Other content data 220 may include indications of medical data 118 to be excluded from diagrams 102, indications of particular graphical layers for placement of particular visible indicia 122, and user input data selecting medical data 118 for inclusion or exclusion from particular diagrams 102.

Figure 3:
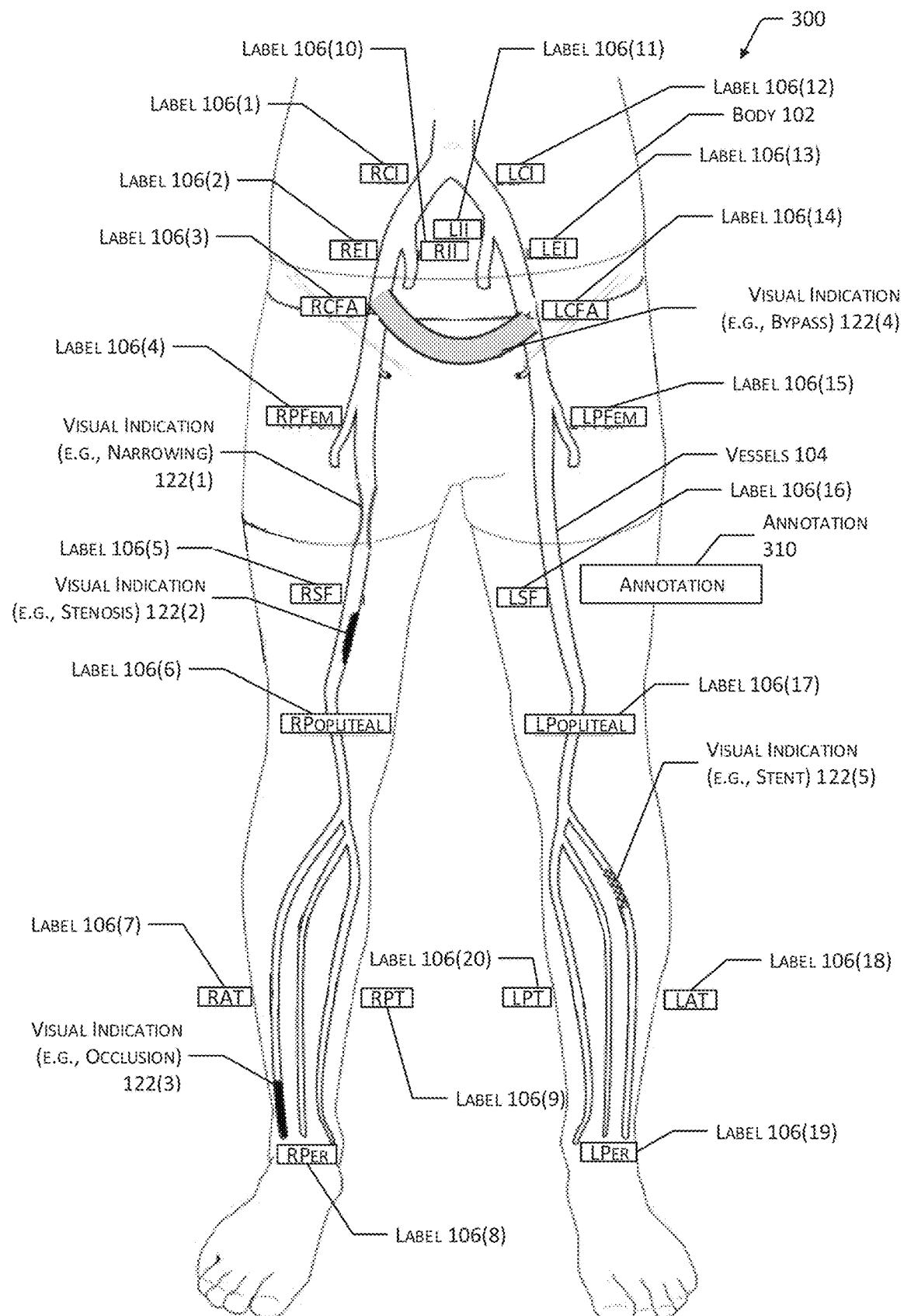
FIG. 3 depicts an example graphical user interface including a diagram having labels, annotations, and other visible indicia based on data determined from one or more reports.

FIG. 3 depicts an example graphical user interface 300 including a diagram 102 having labels 306, annotations 310, and other visible indicia 122 based on data determined from one or more reports 104. The diagram 102 may be included as part of a report 104, or otherwise stored in association with a report 104, and configured for display upon selection by a user, receipt of a query corresponding to a diagram, or other user input. The depicted diagram 102 includes a graphical depiction of the lower extremities of a human body 302 in which anatomical structures (e.g., vessels 304) of a circulatory system are shown. In other implementations, the diagram 102 may include a medical image, such as a scan obtained by examining a patient, instead of a graphical depiction. The particular diagram 102 used in conjunction with a report 104 may be determined based on the content of the report 104. For example, structure data 112 associated with the report 104 may indicate the particular medical structures (e.g., the circulatory system of the lower body) that are the subject of the report. While FIG. 3 depicts an example diagram 102 associated with the vessels 304 of the circulatory system, in other implementations, other anatomical structures or body systems may be depicted.

The diagram 102 may be automatically or manually populated with one or more visible indicia 122, such as labels 306, annotations 310, and so forth. As described with regard to FIGS. 1 and 2, the diagram generation module 120 may provide visible indicia 122 to the diagram 102 based on medical data 118 determined from the associated report(s) 104 and report content data 126 indicating the particular medical data 118 to be depicted and the manner in which the medical data 118 may be reflected in the diagram 102. Mapping data 124 may be used to determine the locations within the diagram 102 at which the visible indicia 122 are provided. In some implementations, one or more of the labels 306, annotations 310, or other visible indicia 122 may be provided to the diagram 102 manually, via user input. For example, a user may interact with the diagram 102 using an input device and provide text to be included in a label 306 or annotation 310. As another example, a user may select a tool corresponding to a medical feature, such as a vessel narrowing, stenosis, occlusion, a bypass, a graft, and so forth. Subsequent interactions with the diagram 102 may include selection of locations in the diagram 102 where visible indicia 122 of the selected medical features may be added, such as the endpoints of a bypass or the location of a graft. Interactions with the diagram 102 may also include selection or input of values corresponding to the medical features, such as dimensions of a bypass or lesion, text annotations 310 describing a graft, and so forth.

The example diagram 102 shown in FIG. 3 includes twenty labels 306, each label 306 indicating a particular vessel 304 within the body 302. A first label 306(1) ("RCI") may indicate the right common iliac artery. A second label 306(2) ("REI") may indicate the right external iliac artery. A third label 306(3) ("RCFA") may indicate the right circumflex artery. A fourth label 306(4) ("RPFem") may indicate the right primary femoral artery. A fifth label 306(5) ("RSF") may indicate the right secondary femoral artery. A sixth label 306(6) ("RPopliteal") may indicate the right popliteal artery. A seventh label 306(7) ("RAT") may indicate the right anterior tibial artery. An eighth label 306(8) ("RPer") may indicate the right peroneal artery. A ninth label 306(9) ("RPT") may indicate the right posterior tibial artery. A tenth label 306(10) ("RII") may indicate the right internal iliac artery. An eleventh label 306(11) ("LII") may indicate the left internal iliac artery. A twelfth label 306(12) ("LCI") may indicate the left common iliac artery. A thirteenth label 306(13) ("LEI") may indicate the left external iliac artery. A fourteenth label 306(14) ("LCFA") may indicate the left circumflex artery. A fifteenth label 306(15) ("LPFem") may indicate the left primary femoral artery. A sixteenth label 306(16) ("LSF") may indicate the left secondary femoral artery. A seventeenth label 306(17) ("LPopliteal") may indicate the left popliteal artery. An eighteenth label 306(18) ("LAT") may indicate the left anterior tibial artery. A nineteenth label 306(19) ("LPer") may indicate the left peroneal artery. A twentieth label 306(20) ("LPT") may indicate the left posterior tibial artery.

In some implementations, visible indicia 122 that relate to features of the diagram 102 that do not depend on data determined from a report 104 may be included as part of the diagram 102 prior to the addition of visible indicia 122 corresponding to the report 104. For example, the labels 306 corresponding to each vessel 304 may be included in the diagram 102 independent of the content of the report 104. In other implementations, certain vessels 304 or other anatomical features may be referenced in a report 104. For example, a report may include alphanumeric data naming one or more vessels 304 or image data depicting one or more vessels 304. Continuing the example, data indicative of particular vessels 304 may be determined from the report 104, such as by identifying values 208 in relevant fields 204, using OCR, text recognition, image recognition, one or more queries or other data mining techniques, and so forth. Labels 306 associated with the referenced vessels 304 may be provided to the diagram 102. The location of one or more of the labels 306 within the diagram 102 may be determined based on one or more of mapping data 124 or report content data 126, as described with regard to FIGS. 1 and 2. For example, a stored diagram 102 indicative of the lower body 302 of a human may include diagram regions 216, defined by coordinates or other methods of differentiation, that correspond to locations of one or more vessels 304, as indicated by the mapping data 124.

In still other implementations, the labels 306 included in a diagram 102 may be determined at least partially based on user input. For example, a user may interact with a report 104 and select one or more fields 204 or values 208 of the report, responsive to which a corresponding visible indication 122 may be provided to the diagram 102. Continuing the example, a user may select portions of a report 104 that relate to the right femoral artery of a patient. Responsive to the user input, the diagram 102 may be populated with labels 306 indicative of the right femoral artery, such as the fourth label 306(4) and the fifth label 306(5). As another example, a user may interact with the diagram 102, such as by selecting a location or depicted anatomical structure and providing user input indicative of a visible indication 122, such as text for addition as a label 306. User input may also be used to modify or remove an existing label 306. In some implementations, at least a portion of the report 104 that corresponds to the added, modified, or removed label 306 may be modified responsive to the user input. For example, when a user selects a region of the diagram 102, that region may be mapped to a portion of a report 104 that corresponds to the part of the body 302 depicted in the region, which may be indicated by the mapping data 124. The modification or addition of a label 306 or other data associated with that region of the diagram 102, via user input, may also cause a modification or addition to be made to the portion of the report 104 that corresponds to the modified region of the diagram 102. For example, one or more regions of the diagram 102 or the mapping data 124 may include an indication of DICOM headers, codes, tags, or other DICOM data. Modification or addition of labels 306 may therefore cause corresponding modifications or additions to a DICOM structured report to be parsed with headers, codes, tags, and so forth associated with the portion of the report 104 affected by the modification or addition of the label(s) 306.

The diagram 102 may also include one or more visible indicia 122 representative of medical features, such as medical or surgical conditions, indicated in the corresponding report 104. The visible indicia 122 may include one or more of a textual (e.g., alphanumeric) annotation or a visible feature within the diagram 102 such as a graphic element. For example, FIG. 1 depicts a first visible indication 122(1) indicative of narrowing in the right femoral artery, shown as two opposing convex arcs. A second visible indication 122(2) may be indicative of stenosis in the right femoral artery, depicted as a shaded area on one side of the associated vessel 304. A third visible indication 122(3) may be indicative of occlusion in the right anterior tibial artery, depicted as a shaded region at the end of the associated vessel 304. A fourth visible indication 122(4) may be indicative of a bypass spanning between the right circumflex artery and the left circumflex artery, depicted as an arc connecting the arteries. A fifth visible indication 122(5) may be indicative of a stent location in the left anterior tibial artery, depicted as a checkered or cross-hatched pattern positioned in the artery. As described with regard to FIGS. 1 and 2, one or more of the visible indicia 122 may be determined based on a report 104. For example, the report 104 may include medical data 118, such as image data, alphanumeric data, or other data indicative of one or more medical findings. The location within the diagram 102 that corresponds to the fields 204 of the report 104 containing the medical data 118 may be determined using the mapping data 124. For example, a stored diagram 102 indicative of the lower body 302 of a human may include regions, defined by coordinates or other location techniques, that correspond to locations of one or more vessels 304 within the diagram 102. Visible indicia 122 representative of medical data 118 may be provided in the diagram 102 at positions corresponding to the locations of the vessels 304, as indicated by the mapping data 124.

In some implementations, the visible indications 122 that are displayed in association with the diagram 102 may be determined at least partially by user input. For example, a user interacting with a report 104 may select or otherwise interact with one or more medical findings. Continuing the example, a user may use a mouse device or other input device to indicate a phrase within a report 104 that reads, "There is 50% stenosis in the right femoral artery." Responsive to the user input indicating this phrase, a visible indication 122 representing stenosis may be provided to the diagram 102 in a region corresponding to the right femoral artery, determined using the mapping data 124. The particular visible indication 122 used to represent stenosis may be determined based on the report content data 126. Other medical findings indicated in a report 104 may similarly be provided to a diagram 102 automatically (e.g., based on medical data 118 indicated in the report content data 126) or based on user input. In some implementations, user input adding, removing, or modifying a portion of a report 104 may also result in corresponding modifications to a diagram 102. For example, a user may edit or provide additional information to a report 104 indicative of one or more medical findings. Responsive to the modification, removal, or addition to the report 104 in a particular field 204, a corresponding visible indication 122 may be provided, modified, or removed at a location in the diagram 102 corresponding to the field 204, as indicated by the mapping data 124.

In other implementations, a user may add visible indicia 122 to one or more regions a diagram 102, which may in turn cause modifications to be made to corresponding portions of a report 104. For example, a user may manually add a visible indication 122 indicative of a graft by selecting two endpoints of the graft. Continuing the example, a user may select a first location with the diagram 102. The first location may be associated with a first femoral artery. A user may then select a second location within the diagram 102 corresponding to a second femoral artery. Responsive to this user input, a visible indication 122 indicative of a Bi-Fem graft may be placed in the selected location(s) within the diagram 102. To define a graft, other user input may also be received. For example, a user may select two points present on two vessels 304, a thickness of the graft, and a point located along the graft. Responsive to this user input, a visible indication 122 indicative of a graft, such as an arc, may be provided to the diagram 102. Based on the mapping data 124, one or more fields 204 of the report 104 that correspond to the regions of the diagram 102 or the type of medical feature indicated by the user input may be determined. A corresponding modification, addition, or removal may be made to the report 104, based at least partially on the user input or the modification(s) to the diagram 102.

As another example, a user may select a location within a vessel 304 for drawing a visible indication 122 indicative of stenosis. The location of the diagram 102 selected by the user (e.g., the proximal, middle, or distal segment of a selected vessel 304), and the severity of the stenosis being drawn (e.g., the dimensions of the area selected by the user) may be determined based on the user input. Responsive to this user input, a visible indication 122 representative of stenosis, having the selected size indicated by the user input, may be provided at the selected location that corresponds to the user input. A modification may also be made to a portion of the report 104 that corresponds to the modified region of the diagram 102, as indicated in the mapping data 124.

As yet another example, a user may select a location with the diagram 102 for drawing a visible indication 122 indicative of a medical feature, such as a lesion. A user may select a point within the diagram 102 as the center of the lesion and provide user input indicative of a radius. In some implementations, points of the lesion located outside of a vessel 304 may be automatically clipped, disregarded, or otherwise modified, such that the lesion is entirely contained within the selected vessel 304. A modification may also be made to a portion of the report 104 that corresponds to the modified region of the diagram 102, as indicated in the mapping data 124.

In one implementation, the graphical user interface 300 associated with the diagram 102 may include one or more tools corresponding to certain medical features. For example, a user may select a "bypass" tool to enable the user to connect two points of the vessels 304. Responsive to the selection of the bypass tool and the two points of the vessels 304, a visible indication 122 indicative of a bypass may be added at the selected locations. Other tools corresponding to other medical findings or features may similarly be provided to a user interface 300. The particular tools provided for selection by a user may be determined based on the content of the report 104 or the diagram 102. In some implementations, the report content data 126 may include indications of the tools to be provided via the user interface 300. In some implementations, background elements and other features of the diagram 102, such as vessel walls or preexisting labels 306, may remain unaffected by the use of the tools to add visible indications 122.

FIG. 3 also depicts an example text annotation 310 in the diagram 102. For example, a user may select a location within the diagram 102 and provide alphanumeric text or other data for inclusion at that location, such as comments regarding medical impressions. In some implementations, the addition or modification of annotations 310 may cause a corresponding modification to be made to the portion(s) of the report 104 that correspond to the region of the diagram 102 where the annotation 310 was provided. In other implementations, text annotations 310 may be provided to a separate portion of the report 104 associated with notes or medical impressions.

In some implementations, measurement values may be populated in a diagram 102, in locations that correspond to the measurement values. Depiction of measurement values in association with parts of the body 302 to which the measurement values correspond may promote an easier understanding of the diagram 102 when compared to a conventional flat table of values.

Figure 4:
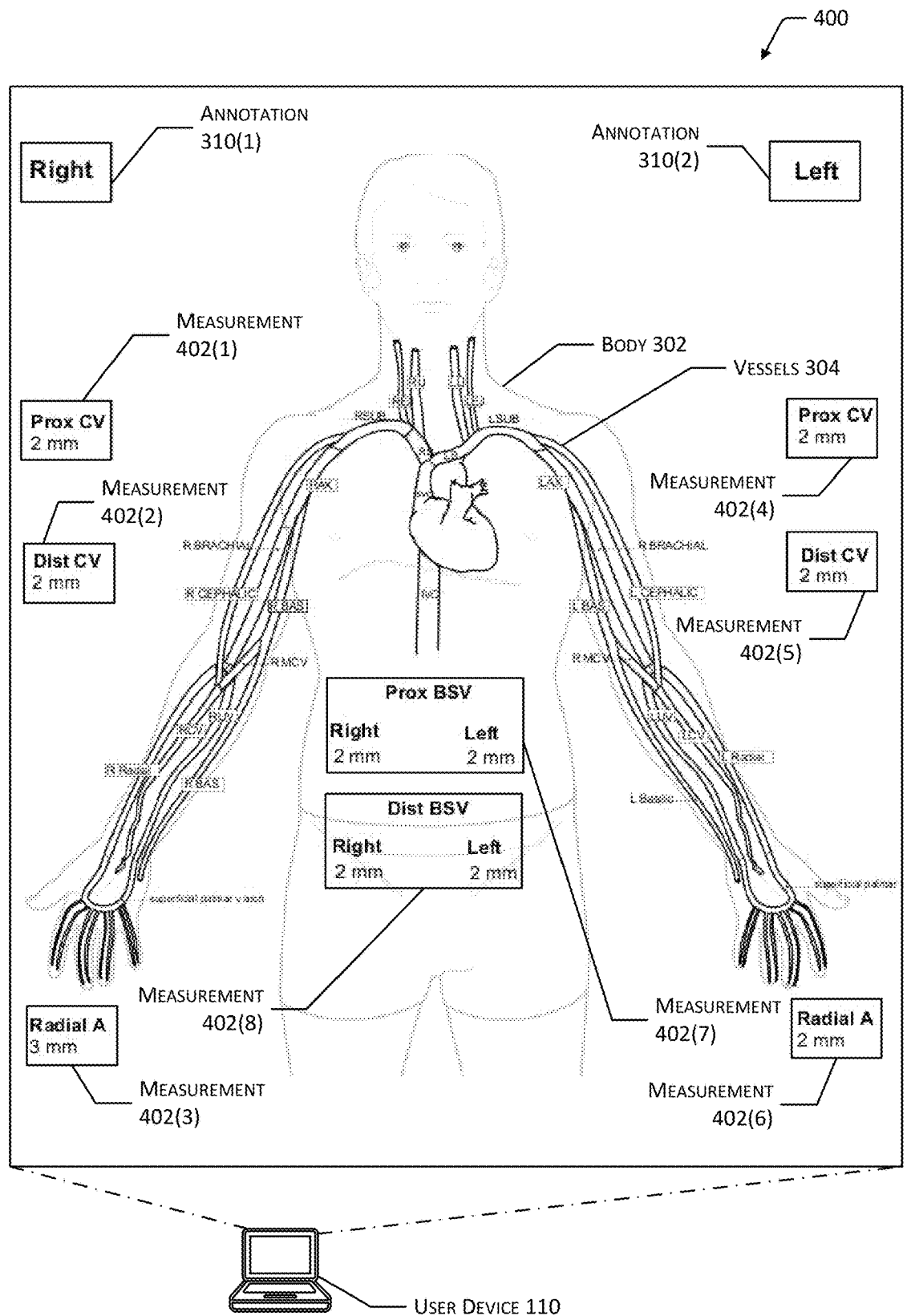
FIG. 4 depicts an example graphical user interface that includes a diagram having annotations and measurements based on data determined from one or more reports.

FIG. 4 depicts an example graphical user interface 400 that includes a diagram 102 having annotations 310 and measurements 402 based on data determined from one or more reports 104. The example diagram 102 illustrates a portion of a human body 302 including vessels 304 of the circulatory system. While FIG. 4 depicts a diagram 102 associated with the circulatory system of the upper body 302 of a patient, in other implementations, diagrams 102 associated with other portions and other systems of the human body 302 may be used.

One or more of the vessels 304 or other portions of the body 302 may have labels 306 or other visible indicia 122 associated therewith, as described with regard to FIG. 3. The diagram 102 may also include one or more annotations 310. For example, a first annotation 310(1) indicates the right side of the depicted body 302, while a second annotation 310(2) indicates the left side of the body 302. The example diagram 102 also includes multiple measurements 402 that correspond to various anatomical features represented at particular regions of the diagram 102. The diagram 102 may be displayed on an output device, such as a display screen of a user device 110, responsive to a query provided by the user device 110 or user input selecting a report 104 or diagram 102.

A first measurement 402(1) and a second measurement 402(2) may include proximal and distal CV measurements, respectively, associated with the right side of the body 302. A third measurement 402(3) may include a radial A measurement associated with the right side of the body. A fourth measurement 402(4) and a fifth measurement 402(5) may include proximal and distal CV measurements, respectively, associated with the left side of the body 302. A sixth measurement 402(6) may include a radial A measurement associated with the left side of the body 302. A seventh set of measurements 402(7) may indicate proximal BSV measurements associated with the right and left sides of the body 302. An eighth set of measurements 402(8) may indicate distal BSV measurements associated with the right and left sides of the body 302.

In some implementations, one or more of the measurements 402 may be determined based on a report 104. For example, a report 104 may include one or more measurement values 208 contained in one or more fields 204. Mapping data 124 that associates portions of the report 104 with regions of the diagram 102 may be used to determine locations within the diagram 102 that correspond to vessels 304 or other anatomical features related to the values 208. A measurement 402 or other visible indication 122 may then be provided to the diagram 102 at the location corresponding to the field 204 of the report 104 from which the value 208 was determined. In some implementations, the diagram 102 may be automatically populated with one or more of the measurements 402 determined from the report 104. For example, report content data 126 may include indications of medical data 118 to be automatically included in one or more diagrams 102. In other implementations, the measurements 402 displayed in association with the diagram 102 may be determined at least partially by user input. For example, a user may select one or more portions of a report 104. Based on the user selection of particular fields 204, values 208, or other data within a report 104, the diagram 102 may be provided with measurements 402 or other visible indicia 122 corresponding to the selected fields 204 or values 208. As another example, a user may select one or more portions of a diagram 102, such as by indicating a particular vessel 304 or other anatomical feature. Responsive to the user input, a portion of the report 104 that corresponds to the selected diagram region 216 may be determined using the mapping data 124. One or more values 208 associated with the determined portion of the report 104 may then be provided to the diagram 102.

In some implementations, user input interacting with one or more measurements 402 or other portions of the diagram 102 may be received. For example, a user may add, remove, or modify one or more measurements 402 or other visible indicia 122. Continuing the example, a user may select a particular vessel 304 and input alphanumeric data indicative of a measurement 402 associated with that vessel 304. Based on the mapping data 124 a portion of the report 104 that corresponds to the selected vessel 304 may be determined, and a value 208 based on the measurement 402 may be provided to the report 104. As another example, a user may modify a value 208 in a report 104. Based on the mapping data 124, a measurement 402 depicted in the diagram 102 that corresponds to the modified value 208 may be determined. The depicted measurement 402 may be modified based on the modification to the value 208 in the report 104.

In some implementations, a single diagram 102 may be generated using multiple reports 104. In other implementations, a single report 104 may be used to generate multiple diagrams 102. Diagrams 102 may contain a vector definition of graphical objects annotated by data corresponding to a portion of a body 302 or other structure and one or more graphical layers. For example, a diagram 102 may include graphical layers corresponding to one or more of: body 302 contour, vessel 304 contour, or measurements 402. Graphical layers corresponding to measurements 402 may also include other content derived from a report 104 or from user input, such as labels 306, annotations 310, or other visible indicia 122. In other implementations, one or more of labels 306, annotations 310, measurements 402, or other visible indicia 122 may correspond to different layers of a diagram 102. For example, a user may elect to view a diagram 102 while suppressing layers that include text annotations 310 from view, but including layers that depict measurements 402. Diagrams 102 one or more identifiers and one or more versions to enable a particular diagram 102 to be stored, retrieved, and distinguished from other diagrams 102 and previous or alternate versions of the particular diagram 102. For example, a first user may annotate or modify a diagram 102 in a first manner, resulting in a first stored version of the diagram 102. A second user may annotate or modify the original diagram 102 in a different manner, resulting in a second stored version of the diagram 102.

Figure 5:
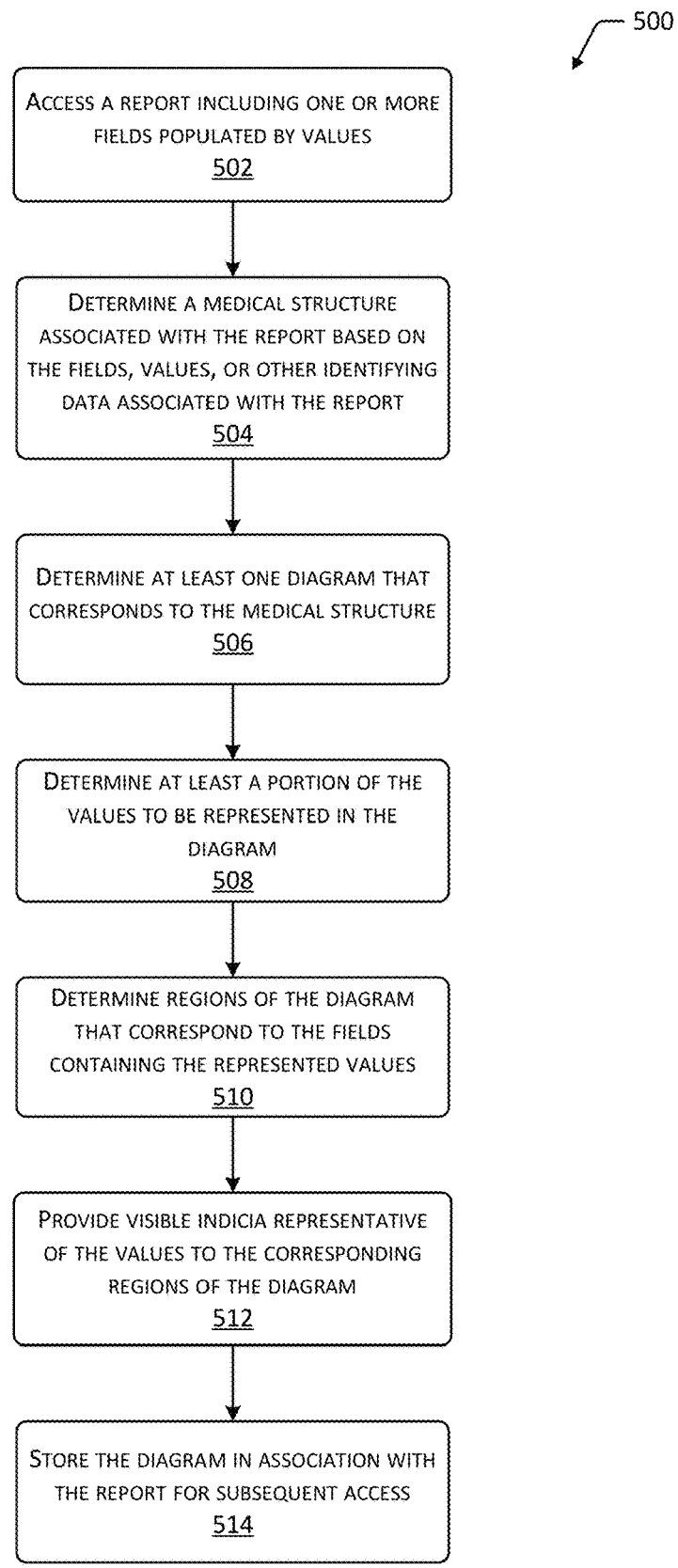
FIG. 5 is a flow diagram illustrating a method for generating one or more diagrams based on one or more reports.

FIG. 5 is a flow diagram 500 illustrating a method for generating one or more diagrams 102 based on one or more reports 104. Block 502 accesses a report 104 including one or more fields 204 populated by values 208. In some implementations, an existing report 104 may be determined, such as by accessing data storage 108 in communication with one or more reporting servers 106. In other implementations, a report 104 may be received from a remote device, such as a user device 110 communicating with the reporting server(s) 106 via one or more networks.

Block 504 determines a medical structure associated with the report 104 based on the fields 204, values 208, or other identifying data associated with the report 104. For example, one or more report identifiers 202, such as a title, header, file name, or other types of identifiers may indicate a medical structure associated with the report 104. As another example, the presence of particular fields 204, such as fields 204 relating to vessel widths or flow rates, may indicate that the report 104 is associated with particular medical structures. As yet another example, the presence of particular values 208 that fall within ranges that correspond to certain medical structures may indicate that the report 104 is associated with those medical structures.

Block 506 determines at least one diagram 102 that corresponds to the medical structure. As described with regard to FIG. 1, a diagram determination module 114 may determine correspondence between structure data 112 of the report 104, indicative of the medical structure, and diagram data 116 that associates structure data 112 with particular diagrams 102. For example, a report 104 associated with a patient's circulatory system would correspond to diagrams 102 that depict one or more portions of the circulatory system, while a report 104 associated with a patient's endocrine system would correspond to diagrams 102 that depict one or more portions of the endocrine system.

Block 508 determines at least a portion of the values 208 to be represented in the diagram 102. In some implementations, all of the values 208 determined from a report 104 may be represented in a diagram 102. In other implementations, report content data 126 may indicate particular medical data 118 to be included in or excluded from diagrams 102. In still other implementations, user input may indicate particular values 208 or other medical data 118 for inclusion in a diagram 102. For example, responsive to selection or indication of a particular field 204, value 208, or other data within a report 104, a diagram 102 may be provided with a visible indication 122 corresponding to the selected field 204, value 208, or data.

Block 510 determines regions of the diagram 102 that correspond to the fields 204 containing the represented values 208. As described with regard to FIGS. 1 and 2, mapping data 124 may associate diagram regions 216 with corresponding identifiers of fields 204 in a report 104. To represent a value 208 from a particular field 204 in a diagram 102, the diagram region 216 that corresponds to the field identifier 206 for the particular field 204 may be determined using the mapping data 124. For example, a value 208 determined from a field 204 associated with the left leg of a patient may map to a diagram region 216 proximate to a depiction of a left leg.

Block 512 provides visible indicia 122 representative of the values 208 to the corresponding regions of the diagram 102. In some implementations, the particular visible indicia 122 used to represent a particular medical feature, object, or value 208 may be determined based on the report content data 126. For example, the report content data 126 may indicate that a particular graphical object is to be used to represent a stent, or that a particular font is to be used when displaying a measurement 402.

Block 514 stores the diagram 102 in association with the report 104 for subsequent access. For example, a user may provide a query associated with a particular diagram 102 or report 104 or a general query associated with particular medical features that may be present in one or more diagrams 102 or reports 104. Responsive to the query, the particular diagram 102 or report 104 may be located, and both the report 104 and corresponding diagram 102 may be out put to the requestor.

Figure 6:
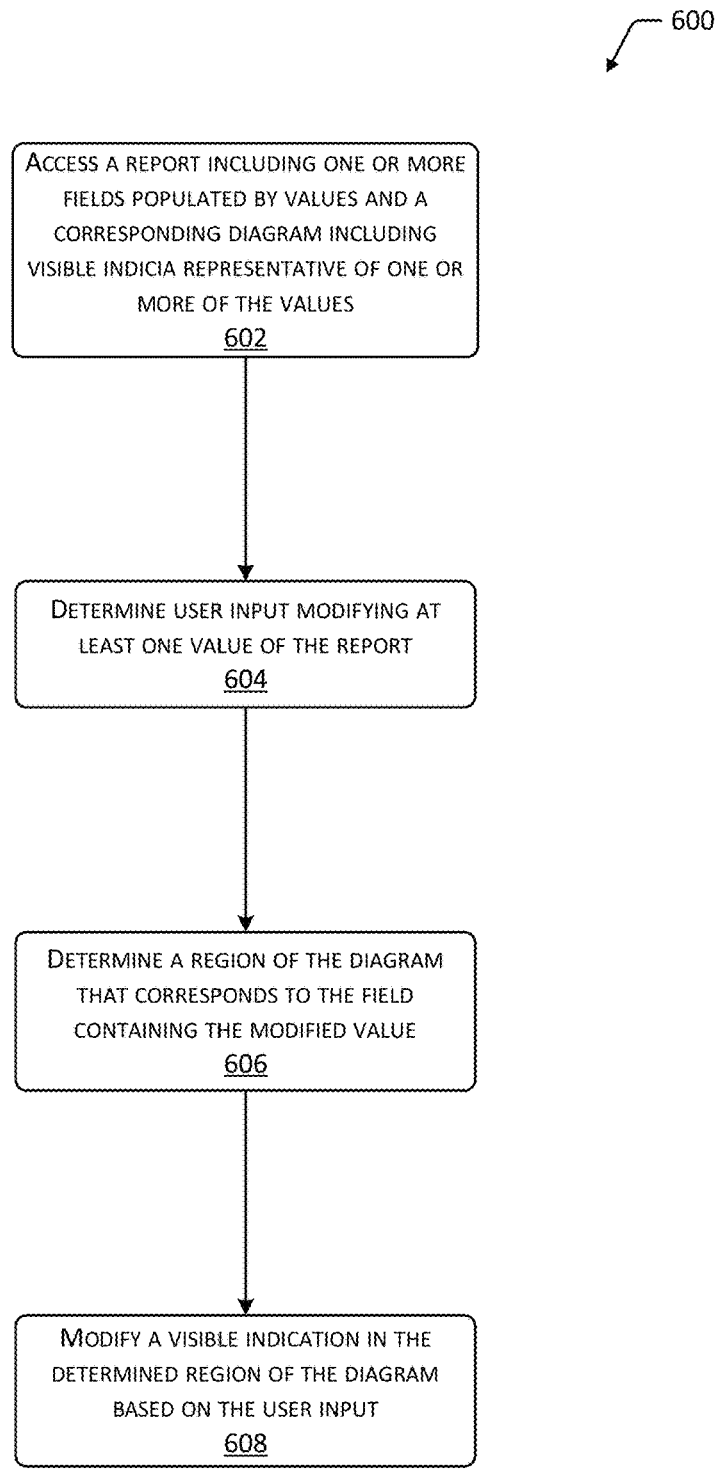
FIG. 6 is a flow diagram illustrating a method for modifying a diagram based on user input modifying one or more reports.

FIG. 6 is a flow diagram 600 illustrating a method for modifying a diagram 102 based on user input modifying one or more reports 104. Block 602 accesses a report 104 including one or more fields 204 populated by values 208 and a corresponding diagram 102 including visible indicia 122 representative of one or more of the values. As described with regard to FIG. 5, a diagram 102 may be stored in association with a report 104 and retrieved responsive to a query or request to access one or more of the report 104 or the diagram 102.

Block 604 determines user input modifying at least one value 208 of the report 104. For example, a user may select a particular field 204 or value 208 and provide one or more of alphanumeric data, image data, or audio data to add, remove, or modify at least a portion of the value 208 associated with the field 204. The report 104 may be modified based on the user input. In some implementations, the modified report 104 may be stored as a different version while the unmodified report 104 is retained.

Block 606 determines a region of the diagram 102 that corresponds to the field 204 containing the modified value 208. As described with regard to FIG. 5, mapping data 124 may associate fields 204 of the report 104 with corresponding regions of the diagram 102. For example, a field 204 that contains a value 208 associated with a patient's aorta may correspond to a diagram region 216 proximate to a depiction of the aorta.

Block 608 modifies a visible indication 122 in the determined region of the diagram 102 based on the user input. For example, if a user deletes a value 208 from a report 104, the visible indication 122 that corresponds to the value 208 may be removed from the diagram 102. If a user modifies the value 208 in the report 104, the visible indication 122 in the diagram 102 may be modified. For example, if a user changes a measurement of a vessel from 3 millimeters (mm) to 2 mm within the report 104, a visible indication 122 that depicts a measurement 402 of "3 mm" may be modified to depict a measurement 402 of "2 mm". If a user adds a value 208 to the report 104, a visible indication 122 may be added to the diagram 102 in a region that corresponds to the field 204 where the value 208 was added, based on the mapping data.

Figure 7:
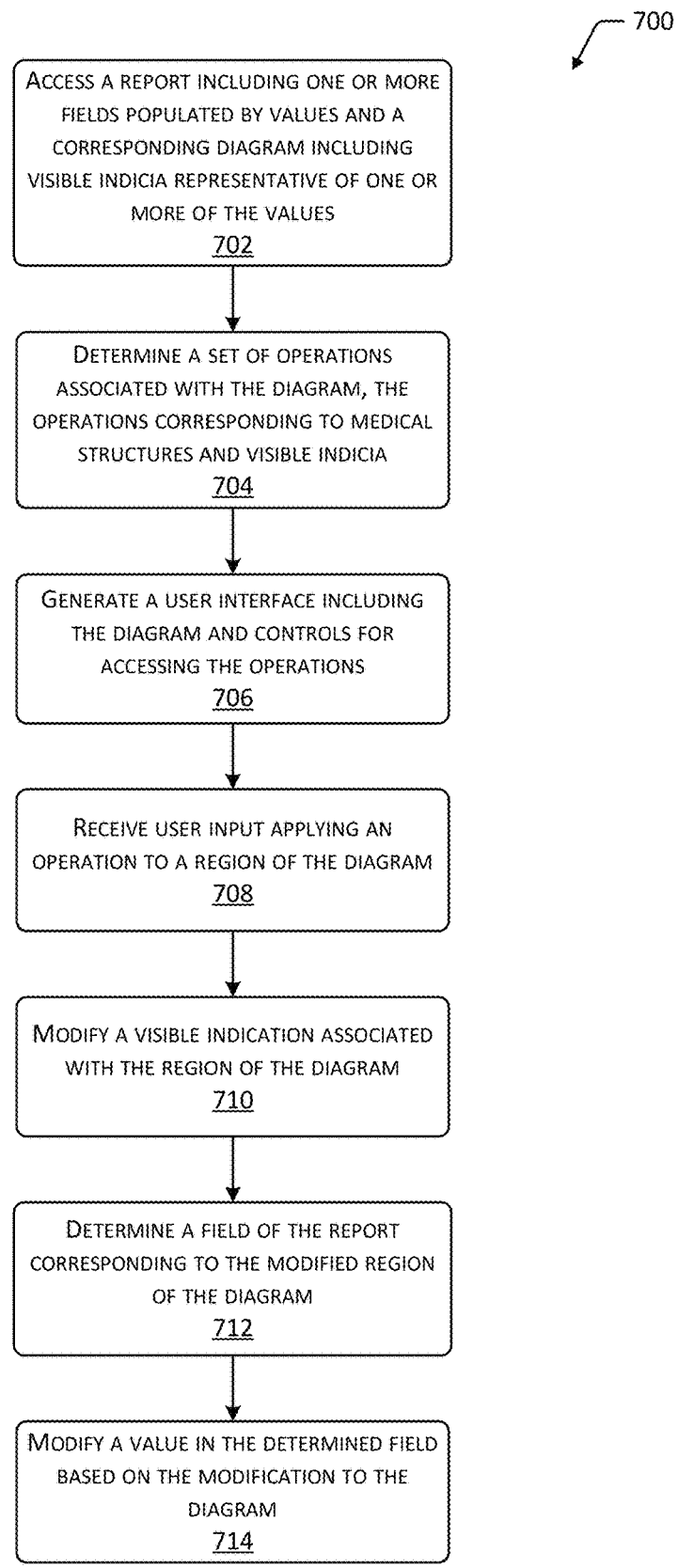
FIG. 7 is a flow diagram illustrating a method for providing a user interface to receive modifications to a diagram and providing corresponding modifications to a report.

FIG. 7 is a flow diagram 700 illustrating a method for providing a user interface to receive modifications to a diagram 102 and providing corresponding modifications to a report 104. Block 702 accesses a repot 104 including one or more fields 204 populated by values 208 and a corresponding diagram 102 including visible indicia 122 representative of one or more of the values 208.

Block 704 determines a set of operations associated with the diagram 102, the operations corresponding to medical structures and visible indicia 122. For example, diagram operations may include tools for adding graphical representations of medical conditions, objects, or structures to a diagram 102. The specific operations or tools associated with a particular diagram 102 may be determined based on the medical structure(s) represented in the diagram 102. For example, a diagram 102 associated with the circulatory system may include tools for adding and modifying bypasses, grafts, stents, lesions, occlusion, stenosis, narrowed vessels, and so forth. Diagrams 102 depicting other body systems or medical structures may be associated with different tools and operations.

Block 706 generates a user interface including the diagram 102 and controls for accessing the operations. For example, the user interface may be configured to receive user input selecting a particular tool, such as a bypass tool. Responsive to selection of the bypass tool, the user interface may be configured to receive user input selecting particular locations within vessels 304 depicted in the diagram 102 as endpoints of the bypass. The user input may also include one or more other parameters, such as a width or shape of the bypass. Responsive to the user input, a visible indication 122 of the bypass may be generated and provided to the diagram 102.

Block 708 receives user input applying an operation to a region of the diagram 102. As another example, the user interface may be configured to receive user input selecting a lesion tool. Responsive to selection of the lesion tool, the user interface may be configured to receive user input selecting a particular location associated with a vessel 304 in the diagram 102 as the location of the center of the lesion. The user input may also include one or more other parameters, such as a radius of the lesion. The lesion tool may be configured to disregard to remove portions of the lesion that extend beyond the boundaries of a vessel 304 when generating a corresponding visible indication 122 for inclusion in the diagram 102.

Block 710 modifies a visible indication 122 associated with the region of the diagram 102 based on the user input. As yet another example, the user interface may be configured to receive user input selecting a graft tool. Responsive to selection of the graft tool, the user interface may be configured to receive user input selecting two points positioned on vessels 304 in the diagram 102. The user input may also include one or more other parameters, such as a thickness of the graft and a point along the graft. Responsive to the user input, a visible indication 122 of the graft may be generated and provided to the diagram 102. In a similar manner, user input may be used to modify existing visible indicia 122 or remove existing visible indicia 122.

Block 712 determines a field 204 of the report 104 corresponding to the modified region of the diagram 102. As described with regard to FIGS. 5 and 6, mapping data 124 may associate particular fields 204 of the report 104 with corresponding regions of the diagram 102. Block 714 modifies a value 208 in the determined field 204 based on the modification to the diagram 102. For example, responsive to the addition of a graft to a particular region of the diagram 102 corresponding text may be added to a field 204 of the report 104 where the presence of a graft would typically by notated.

Figure 8:
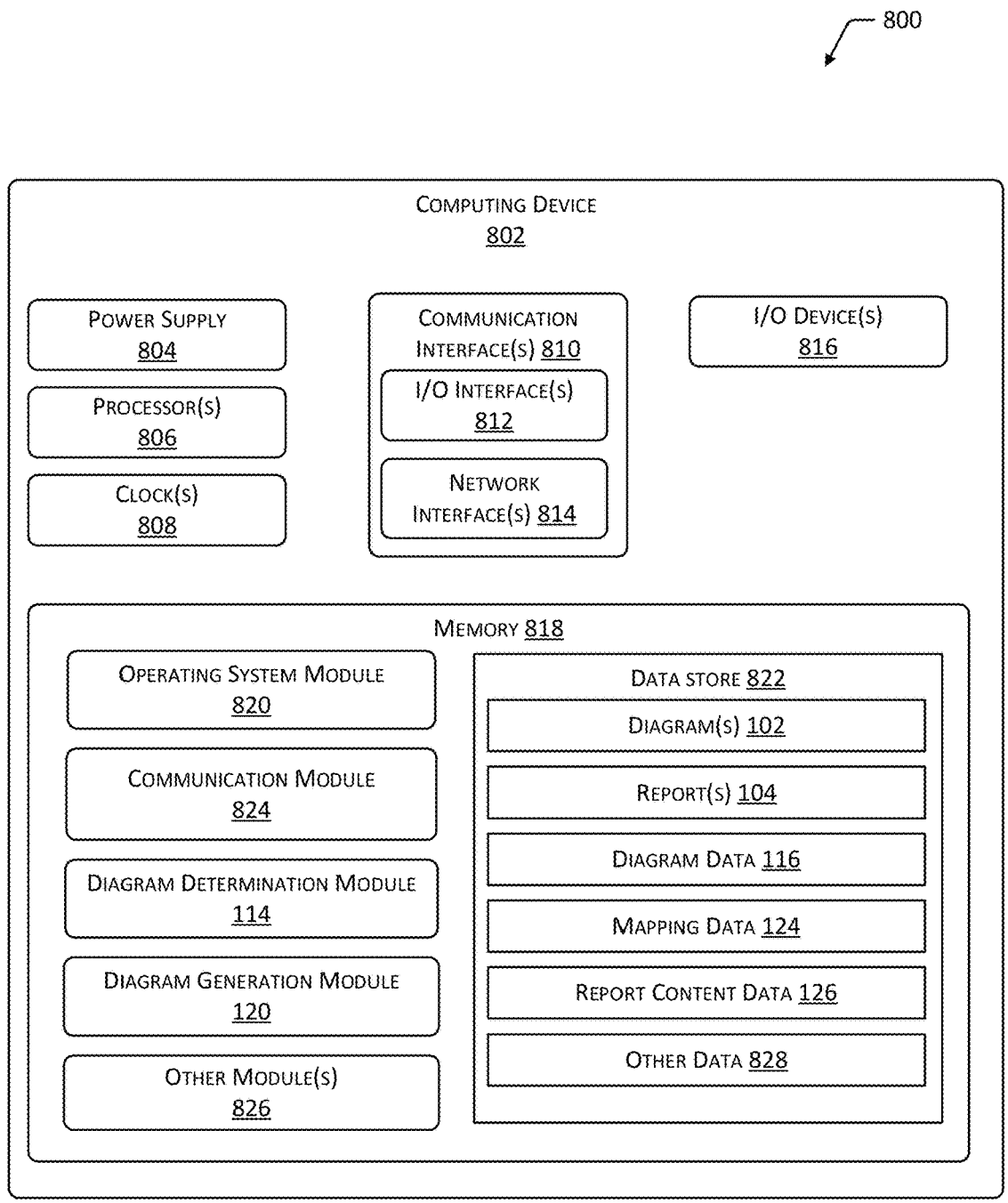
FIG. 8 is a block diagram depicting a computing device within the scope of the present disclosure.

FIG. 8 is a block diagram depicting 800 a computing device 802 within the scope of the present disclosure. The computing device 802 may include one or more of: the reporting server(s) 106 described with regard to FIG. 1, other computing devices 802 in communication therewith, or other computing devices 802 configured to perform the functions described with regard to the reporting server(s) 106. For example, one or more user devices 110 or other associated computing devices 802 may be configured to perform at least a portion of the functions of the reporting server(s) 106.

One or more power supplies 804 may be configured to provide electrical power suitable for operating the components of the computing device 802. In some implementations, the power supply 804 may include a rechargeable battery, fuel cell, photovoltaic cell, power conditioning circuitry, and so forth.

The computing device 802 may include one or more hardware processor(s) 806 (processors) configured to execute one or more stored instructions. The processor(s) 806 may include one or more cores. One or more clocks 808 may provide information indicative of date, time, ticks, and so forth. For example, the processor(s) 806 may use data from the clock(s) 808 to generate a timestamp, trigger a preprogrammed action, and so forth.

The computing device 802 may include one or more communication interfaces 810, such as input/output (I/O) interfaces 812, network interfaces 814, and so forth. The communication interfaces 810 may enable the computing device 802, or components of the computing device 802, to communicate with other computing devices 802 or components of the other computing devices 802. The I/O interfaces 812 may include interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 812 may couple to one or more I/O devices 816. The I/O devices 816 may include any manner of input device or output device associated with the computing device 802. For example, I/O devices 816 may include touch sensors, keyboards, mouse devices, microphones, image sensors (e.g., cameras), scanners, displays, speakers, haptic devices, printers, and so forth. In some implementations, the I/O devices 816 may be physically incorporated with the computing device 802 or may be externally placed.

The network interfaces 814 may be configured to provide communications between the computing device 802 and other devices, such as the I/O devices 816, routers, access points, and so forth. The network interfaces 814 may include devices configured to couple to one or more networks including LANs, wireless LANs, WANs, wireless WANs, and so forth. For example, the network interfaces 814 may include devices compatible with Ethernet, Wi-Fi®, Bluetooth®, ZigBee®, Z-Wave, 3G, 4G, LTE, and so forth.

The computing device 802 may include one or more busses or other internal communications hardware or software that allows for the transfer of data between the various modules and components of the computing device 802.

As shown in FIG. 8, the computing device 802 may include one or more memories 818. The memory 818 may include one or more CRSM. The CRSM may be any one or more of an electronic storage medium, a magnetic storage medium, an optical storage medium, a quantum storage medium, a mechanical computer storage medium, and so forth. The memory 818 may provide storage of computer-readable instructions, data structures, program modules, and other data for the operation of the computing device 802. A few example modules are shown stored in the memory 818, although the same functionality may alternatively be implemented in hardware, firmware, or as a system on a chip (SoC).

The memory 818 may include one or more operating system (OS) modules 820. The OS module 820 may be configured to manage hardware resource devices such as the I/O interfaces 812, the network interfaces 814, the I/O devices 816, and to provide various services to applications or modules executing on the processors 806. The OS module 820 may implement a variant of the FreeBSD™ operating system as promulgated by the FreeBSD Project; UNIX™ or a UNIX-like operating system; a variation of the Linux™ operating system as promulgated by Linus Torvalds; the Windows® operating system from Microsoft Corporation of Redmond, Wash., USA; or other operating systems.

A data store 822 and one or more of the following modules may also be stored in the memory 818. The modules may be executed as foreground applications, background tasks, daemons, and so forth. The data store 822 may use a flat file, database, linked list, tree, executable code, script, or other data structure to store information. In some implementations, the data store 822 or a portion of the data store 822 may be distributed across one or more other devices including other computing devices 802, network attached storage devices, and so forth.

A communication module 824 may be configured to establish communications with one or more other computing devices 802, such as user devices 110 or data storage 108 remote from the computing device 802. The communications may be authenticated, encrypted, and so forth.

The memory 818 may store the diagram determination module 114. The diagram determination module 114 may determine particular diagrams 102 that correspond to reports 104. For example, structure data 112 determined from a report 104 may indicate one or more medical structures associated with the report 104. Diagram data 116 in the data store 822 may associate structure data 112 with various diagrams 102. The diagram determination module 114 may determine correspondence between at least a portion of the structure data 112 from a report 104 and at least a portion of the diagram data 116 to determine at least one diagram 102 that corresponds to the report 104. In some implementations, multiple diagrams 102 may correspond to a single report 104 or multiple reports 104 may correspond to a single diagram 102.

The memory 818 may also store the diagram generation module 120. The diagram generation module 120 may modify diagrams 102 determined by the diagram determination module 114 based on one or more of: medical data 118 determined from the report 104, modifications to the report 104, or user input. For example, a report 104 may include medical data 118 such as values 208 associated with one or more medical structures. The diagram generation module 120 may determine at least a portion of the medical data 118 to be included in a diagram 102, based on report content data 126, and a region of the diagram 102 that corresponds to the determined portion of the medical data 118, based on mapping data 124. The diagram generation module 120 may then provide a visible indication 122 of the medical data 118 to the determined region of the diagram 102. As another example, the diagram generation module 120 may determine use input modifying, adding, or removing one or more values 208 of the report 104. Based on the mapping data 124, the diagram generation module 120 may determine a region of the diagram 102 that corresponds to the modified portion of the report 104. The diagram generation module 120 may then modify, add, or remove one or more visible indicia 122 at the region of the diagram 102 based on the user input. As yet another example, user input interacting with the diagram 102 may be determined. User input may include the selection of tools or operations associated with the diagram 102, the indication of one or more regions of the diagram 102, the input of parameters corresponding to medical features, the input of measurements 402, text annotations 310, labels 306, and so forth. The diagram generation module 120 may add, remove, or modify one or more visible indicia 122 within the diagram 102 based on the user input. In some implementations, based on the mapping data 124, the diagram generation module 120, or another module, may determine a portion of the report 104 that corresponds to the modified region of the diagram 102, and add, remove, or modify a value 208 within the corresponding portion of the report 104 based on the user input.

In some implementations, diagrams 102 may be generated using a Scalable Vector Graphics (SVG) image format, such as the format set forth by the World Wide Web Consortium (W3C) in 1999. For example, a diagram 102 may be generated using the latest SVG version (SVG draft), set forth in 2015. Use of a standard format, such as SVG, may allow standard editing tools to be used to modify the diagrams 102. Additionally, SVG includes use of Extensible Markup Language (XML), which may enable diagrams 102 to be enriched with additional information identifying one or more elements within the diagrams 102. The additional information may include computer-readable information that may enable identification of the elements by one or more computing devices 802.

In some implementations, the diagrams 102 may include multiple graphical layers, the visibility of which may be toggled. For example, measurements 402 may be included in a first layer. Body contours such as vessels 304 or portions of a depicted body 302 may be included in a second layer. Labels 306 may be included in a third layer.

In one implementation, one layer, a "vessel-guide" layer, may include a path comprising Bezier curves that correspond to the middle of the depicted vessels 304. This vessel-guide layer may facilitate determination of the position and direction of the vessel 304 when one or more tools are used to interact with the diagram 102. For example, a stent may be represented by a visible indication 122 having a rectangular shape that is oriented along a vessel 304. To position a visible indication 122 of the stent within a vessel 304 in a diagram 102, the vessel-guide layer may be used to determine a vector parallel with the vessel 304 at each point of the vessel length along which the stent is placed. When user input regarding placement of a visible indication 122 of a stent within a depicted vessel 304 is received, the vessel-guide layer may be used to automatically position the representation of the stent within the vessel 304 in a manner that follows the shape of the vessel 304. Use of the vessel-guide layer may eliminate the need to calculate a vector using the two opposite edges of the vessel 304, which may have different shapes, which may fork, and so forth. In some implementations, a user may move or reshape a vessel 304, such as when a user attempts to display a narrowing or dilation of the vessel 304. Modification of the vessel 304 may include determination of additional control points corresponding to the modified vessel 304 and resampling of the Bezier curve corresponding to the original path of the vessel 304. Movement or reshaping of the vessel 304 may result in a change to the corresponding vector of the vessel-guide layer of the diagram 102.

In some implementations, one or more vessels 304 or other portions of a body 302 may be drawn or defined as a polygon or other closed form, having boundaries. If a user input, such as a button press of a mouse device, is executed while a mouse pointer is within a polygon corresponding to a particular vessel 304, this input may be applied to that vessel 304. Polygons may have an associated SVG identifier, which may be stored in association with a corresponding portion of the structured report, such that a user interaction with a particular polygon may be mapped to a corresponding portion of the structured report. The boundaries of a vessel 304 or other portion of the body 302 may also be used to determine clipping paths associated with graphical representations and user tools. For example, a visible indication 122 of a lesion, drawn by a user, may be clipped to remove portions of the drawn lesion that are outside of a vessel 304. In a similar manner, if a user modifies the shape of a vessel 304, the boundaries of the corresponding polygon may be modified to correspond with the new shape. In some implementations, portions of an existing visible indication 122 that are external to the boundaries of the new polygon may be removed from the diagram 102.

Other graphical representations may also be affected by the boundaries of the polygons corresponding to one or more vessels 304. For example, by drawing a bypass, a new vessel 304 may be created. The new vessel 304 may be defined by a set of Bezier curves corresponding to a path of the vessel 304, a polygon corresponding to boundaries of the vessel 304, and one or more identifiers that may be mapped to corresponding portions of the report 104 that relate to the vessel 304. When a graft is drawn, the names (e.g., labels 306 or corresponding SVG identifiers) of the vessels 304 used as the anastomosis for the graft may be known and mapped to a corresponding portion of the report 104. An attempt to create a graft not connected to any vessel 304 may be prevented by preventing placement of the anastomosis outside of the boundaries of the polygon defining the vessel 304.

One or more labels 306, measurements 402, annotations 310, and so forth may have an associated a SVG identifier. The identifier(s) may indicate which of the depicted elements are labels 306, which are measurements 402, which are annotations 310, and may further indicate relationships between elements. For example, an area of the diagram 102 that includes a textual label 306 may also include an adjacent area depicting a measurement 402 that corresponds to the structure associated with the label 306. The SVG identifiers of that particular label 306 and measurement 402 may be related, such that if one of the measurement 402 or the label 306 is deleted or hidden from view, the other may also be deleted or hidden. The SVG identifiers may also be indicative of a corresponding portion of a report 104. For example, a SVG identifier for a depicted measurement 402 for brachial artery peak systolic velocity may correspond to a textual component of a report 104 where the value 208 for the brachial artery peak systolic velocity is recorded. If the value for brachial artery peak systolic velocity is modified in either the report 104 or the diagram 102, the corresponding element may also be automatically modified. SVG identifiers may also indicate one or more characteristics of the corresponding element. For example, a SVG identifier may include label conventions for an element, mapping between names and report codes, and so forth.

Other modules 826 may also be present in the memory 818. For example, user interface modules may be used to provide user interfaces depicting diagrams 102 and tools or operations associated with the diagrams 102 to user devices 110. User interface modules may also receive user input via the user interfaces. Encryption modules may be used to encrypt and decrypt communications between computing devices 802. Authentication modules may be used to authenticate communications sent or received by computing devices 802.

Other data 828 within the data store 822 may include user input data, such as configurations and settings associated with computing devices 802 or user input selecting medical data 118 to be used as report content data 126 for generating diagrams 102. Other data 828 may include security data, such as encryption keys and schema, access credentials, and so forth. Other data 828 may also include sets of operations or tools associated with particular diagrams 102. For example, tools used to provide or modify visible indicia 122 associated with a diagram 102 of the circulatory system (e.g., lesion, graft, or bypass tools) may not be associated with diagrams 102 that depict the endocrine system. However, the diagrams 102 of the endocrine system may include other tools or operations not associated with diagrams 102 depicting the circulatory system.

In different implementations, different computing devices 802 may have different capabilities or capacities. For example, reporting servers 106 may have significantly more processor 806 capability and memory 818 capacity compared to the processor 806 capability and memory 818 capacity of user devices 110.

The processes discussed in this disclosure may be implemented in hardware, software, or a combination thereof. In the context of software, the described operations represent computer-executable instructions stored on one or more computer-readable storage media that, when executed by one or more hardware processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described in this disclosure. The computer-readable storage medium may be one or more of an electronic storage medium, a magnetic storage medium, an optical storage medium, a quantum storage medium, and so forth. For example, the computer-readable storage media may include, but is not limited to, hard drives, floppy diskettes, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Although certain steps have been described as being performed by certain devices, software programs, processes, or entities, this need not be the case, and a variety of alternative implementations will be understood by those having ordinary skill in the art.

Additionally, those having ordinary skill in the art readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as exemplary forms of implementing the claims.

What is claimed is:

1. A system comprising:
   one or more non-transitory computer readable storage media storing computer-executable instructions; and
   one or more hardware processors configured to execute the computer-executable instructions to:
      access a report stored in one or more memories, the report including structure data indicative of a medical structure and medical data that includes alphanumeric data indicative of one or more values or characteristics associated with the medical structure;
      determine, based on the structure data, the medical structure that is associated with the report;
      access diagram data stored in the one or more memories, wherein the diagram data associates the medical structure with a diagram;
      determine that the diagram data associates the medical structure of the report with the diagram, thereby indicating that the diagram depicts at least a portion of the medical structure of the report;
      access mapping data associated with the diagram, wherein the mapping data associates the one or more values or characteristics of the report with one or more regions of the diagram;
      determine, based on the mapping data, a region of the diagram that corresponds to a value included in the alphanumeric data; and
      provide a visible indication of the value of the alphanumeric data to the region of the diagram such that the diagram presents the visible indication in association with a portion of the medical structure.

2. The system of claim 1, further comprising computer-executable instructions to:
   receive user input modifying the value included in the medical data of the report;
   determine, based on the mapping data, the region of the diagram that corresponds to the value; and
   modify the visible indication provided to the region of the diagram based at least partially on the user input.

3. The system of claim 1, further comprising computer-executable instructions to:
   determine one or more operations associated with the diagram;
   provide a user interface presenting the diagram and an indication of the one or more operations;
   receive user input via the user interface selecting an operation of the one or more operations, wherein the operation is configured to one or more of: modify the visible indication or add a second visible indication to at least one region of the diagram;
   receive user input selecting the at least one region of the diagram;
   receive user input indicative of at least one parameter associated with the operation;
   based on the user input selecting the at least one region and the user input indicative of the at least one parameter, modify the at least one region of the diagram;
   determine, based on the mapping data, a portion of the medical data that corresponds to the at least one region of the diagram; and
   modify the portion of the medical data of the report based at least partially on the user input indicative of the at least one parameter.

4. The system of claim 1, further comprising computer-executable instructions to:
   receive user input indicative of the region of the diagram;
   receive user input indicative of one or more of a characteristic or a value associated with the medical structure;
   access report content data that associates a characteristic of the medical structure with one or more visible indicia;
   based on the report content data, determine the one or more visible indicia that correspond to the characteristic of the medical structure;
   provide the region of the diagram with the one or more visible indicia that correspond to the characteristic of the medical structure;
   determine, based on the mapping data, the value of the report that corresponds to the region of the diagram; and
   modify the value of the report based at least partially on the user input.

5. The system of claim 1, further comprising computer-executable instructions to:
   receive user input selecting one or more values associated with at least one region of the diagram;
   determine, based on the mapping data, a portion of the report that corresponds to the at least one region of the diagram; and
   modify the portion of the report to include the one or more values.

6. The system of claim 1, further comprising computer-executable instructions to:
   receive user input selecting one or more values of the report;
   determine, based on the mapping data, at least one region of the diagram that corresponds to the one or more values of the report; and
   modify the at least one region of the diagram to include the one or more values.

7. A system comprising:
   one or more non-transitory computer readable storage media storing computer-executable instructions; and
   one or more hardware processors configured to execute the computer-executable instructions to:
      access a diagram that is stored in association with a report that includes alphanumeric data indicative of one or more values;
      receive user input associated with a region of the diagram;

access mapping data associated with the diagram, wherein the mapping data associates the region of the diagram with a value of the one or more values of the report;

based on the mapping data, determine that the value of the report corresponds to the region of the diagram; and modify the value of the report based at least partially on the user input.

8. The system of claim 7, wherein the computer-executable instructions to receive the user input associated with the region of the diagram comprise computer-executable instructions to:

receive user input indicative of a type of medical feature; and receive user input indicative of at least one parameter corresponding to the type of medical feature, the system further comprising computer-executable instructions to:

access report content data that associates one or more of the type of medical feature or the at least one parameter with a visible indication;

based on the report content data, determine the visible indication that corresponds to the one or more of the type of medical feature or the at least one parameter; and add the visible indication in association with the region of the diagram.

9. The system of claim 8, wherein the user input indicative of the at least one parameter includes an indication of the region of the diagram associated with the medical feature, and the visible indication is generated proximate to the region.

10. The system of claim 8, wherein the user input indicative of the at least one parameter includes a selection of the region of the diagram and alphanumeric data associated with the medical feature, and the visible indication includes the alphanumeric data proximate to the region of the diagram.

11. The system of claim 8, further comprising computer-executable instructions to:

determine medical data that corresponds to one or more of the visible indication or the user input, wherein the medical data is indicative of one or more values or characteristics associated with the type of medical feature; and provide an indication of the medical data to the report.

12. The system of claim 8, further comprising computer-executable instructions to:

receive a query including an indication of one or more of the type of medical feature or the visible indication;

determine that the diagram includes the one or more of the type of medical feature or the visible indication; and generate a response to the query that indicates one or more of the diagram or the report that is stored in association with the diagram.

13. A system comprising:

one or more non-transitory computer readable storage media storing computer-executable instructions; and one or more hardware processors configured to execute the computer-executable instructions to:

access a report including medical data indicative of one or more values or characteristics associated with a medical structure;

access diagram data that associates the medical structure of the report with a diagram;

based on the diagram data, determine that the diagram corresponds to the medical structure associated with the report;

receive user input that one or more of adds, modifies, or selects a particular value or characteristic of the report;

determine a portion of the report associated with the user input;

access mapping data associated with the diagram, wherein the mapping data associates a region of the diagram with the portion of the report;

based on the mapping data, determine the region of the diagram that corresponds to the portion of the report; and provide a visible indication of the particular value or characteristic to the region of the diagram.

14. The system of claim 13, further comprising computer-executable instructions to:

receive user input modifying alphanumeric data representing the particular value or characteristic;

based on the mapping data, determine the region of the diagram that corresponds to the portion of the report associated with the particular value or characteristic; and modify the visible indication associated with the region of the diagram based at least in part on the user input.

15. The system of claim 13, further comprising computer-executable instructions to:

receive user input indicative of the region of the diagram;

receive user input modifying one or more of the visible indication or the region of the diagram;

based on the mapping data, determine the portion of the report that corresponds to the region of the diagram; and modify the portion of the report based at least in part on the user input modifying the one or more of the visible indication or the region of the diagram.

16. The system of claim 13, further comprising computer-executable instructions to:

receive user input indicative of a type of medical feature;

receive user input indicative of one or more regions of the diagram associated with the type of medical feature;

receive user input indicative of at least one parameter associated with the medical feature; and provide the one or more regions of the diagram with a second visible indication indicative of the medical feature.

17. The system of claim 16, further comprising computer-executable instructions to:

determine report content data associated with one or more of: the type of medical feature, the one or more regions of the diagram, or the at least one parameter;

determine, based on the mapping data, one or more portions of the report that correspond to the one or more regions of the diagram; and provide the one or more portions of the report with information indicative of the report content data.

18. The system of claim 13, further comprising computer-executable instructions to:

receive a query including an indication of one or more of the visible indication, the particular value or characteristic, or the region of the diagram;

determine that the diagram includes the one or more of the visible indication, the particular value or characteristic, or the region;

generate an output indicative of one or more of the diagram or the report; and provide the output responsive to the query.

19. The system of claim 13, wherein the visible indication includes alphanumeric data indicative of a value associated with at least a portion of the medical structure proximate to the region of the diagram.

20. The system of claim 13, wherein the visible indication includes image data indicative of a medical condition associated with at least a portion of the medical structure proximate to the region of the diagram.

\* \* \* \* \*